(12) United States Patent
Nakamura et al.

(10) Patent No.: US 9,345,430 B2
(45) Date of Patent: May 24, 2016

(54) IMAGING APPARATUS AND IMAGING METHOD THEREOF, IMAGE PROCESSING APPARATUS AND IMAGE PROCESSING METHOD THEREOF, AND PROGRAM

(71) Applicant: Sony Corporation, Tokyo (JP)

(72) Inventors: Yusuke Nakamura, Kanagawa (JP); Shinichiro Gomi, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 14/446,858

(22) Filed: Jul. 30, 2014

(65) Prior Publication Data
US 2015/0062380 A1 Mar. 5, 2015

(30) Foreign Application Priority Data
Aug. 27, 2013 (JP) .................. 2013-175770

(51) Int. Cl.
*A61B 5/00* (2006.01)
*G06T 7/00* (2006.01)
*G06K 9/00* (2006.01)
*G01N 21/21* (2006.01)

(52) U.S. Cl.
CPC .............. *A61B 5/441* (2013.01); *A61B 5/0077* (2013.01); *G06T 7/0012* (2013.01); *A61B 2576/00* (2013.01); *G01N 21/21* (2013.01); *G06K 9/00885* (2013.01); *G06T 2207/10152* (2013.01); *G06T 2207/30088* (2013.01)

(58) Field of Classification Search
CPC .. A61B 5/441; A61B 5/0077; A61B 2576/00; G06T 7/0012; G06T 2207/10152; G06T 2207/30088; G06K 9/00885

USPC .......................................... 348/370
See application file for complete search history.

(56) References Cited

U.S. PATENT DOCUMENTS

| 2009/0043363 A1* | 2/2009 | Cotton ................... A61B 5/442 607/88 |
| 2013/0188023 A1* | 7/2013 | Kuang .............. H01L 27/14621 348/49 |

FOREIGN PATENT DOCUMENTS

JP 2010-273737 12/2010

* cited by examiner

*Primary Examiner* — Gevell Selby
(74) *Attorney, Agent, or Firm* — Michael Best & Friedrich LLP

(57) ABSTRACT

An imaging apparatus includes: an unpolarized light-emitting portion configured to emit light having an unpolarized component; a polarized light-emitting portion configured to emit light having a predetermined polarized component via a first polarization filter; and an imaging element configured to image a subject, which is irradiated with light by one of the unpolarized light-emitting portion and the polarized light-emitting portion, through a second polarization filter, the first polarization filter and the second polarization filter having polarization directions in an orthogonal relationship to each other, the imaging element being further configured to image the subject irradiated with light by the unpolarized light-emitting portion and the subject irradiated with light by the polarized light-emitting portion in a time division manner and output an unpolarized light image and an orthogonal polarized light image that are obtained as a result of imaging.

20 Claims, 29 Drawing Sheets

IMAGING APPARATUS AND IMAGING METHOD THEREOF, IMAGE PROCESSING APPARATUS AND IMAGE PROCESSING METHOD THEREOF, AND PROGRAM

CROSS REFERENCE TO RELATED APPLICATIONS

This application claims the benefit of Japanese Priority Patent Application JP 2013-175770 filed Aug. 27, 2013, the entire contents of which are incorporated herein by reference.

BACKGROUND

The present disclosure relates to an imaging apparatus and an imaging method thereof, an image processing apparatus and an image processing method thereof, and a program, and in particular to an imaging apparatus and an imaging method thereof, an image processing apparatus and an image processing method thereof, and a program, that enable a skin surface condition to be evaluated with a lower-cost configuration.

Methods of analyzing a skin surface condition, for example, a skin shine value and skin texture have been studied. For example, there has been proposed a method of preparing polarization filters on a light source side and an image sensor side to provide a parallel polarized state and an orthogonal polarized state, imaging a skin in each of the states, and calculating a skin shine value based on a difference therebetween (e.g., see Japanese Patent Application Laid-open No. 2010-273737 (hereinafter, referred to as Patent Document 1).

SUMMARY

In order to realize the method above, it is necessary to prepare three (three kinds of) polarization filters, place two of the three polarization filters on the light source side to provide two kinds of polarization of the parallel polarized polarization and the orthogonal polarization, and place one of the three polarization filters on the image sensor side. Alternatively, it is necessary to prepare two (two kinds of) polarization filters and place the polarization filters on the light source side and the image sensor side, respectively, and a mechanism for performing imaging with either the light source or the image sensor being rotated at 90 degrees is also necessary. Therefore, it is desirable to provide a method by which the skin surface condition can be evaluated at lower costs.

In view of the above-mentioned circumstances, it is desirable to evaluate a skin surface condition with a lower-cost configuration.

According to the first embodiment of the present disclosure, there is provided an imaging apparatus including: an unpolarized light-emitting portion configured to emit light having an unpolarized component; a polarized light-emitting portion configured to emit light having a predetermined polarized component via a first polarization filter; and an imaging element configured to image a subject, which is irradiated with light by one of the unpolarized light-emitting portion and the polarized light-emitting portion, through a second polarization filter, the first polarization filter and the second polarization filter having polarization directions in an orthogonal relationship to each other, the imaging element being further configured to image the subject irradiated with light by the unpolarized light-emitting portion and the subject irradiated with light by the polarized light-emitting portion in a time division manner and output an unpolarized light image and an orthogonal polarized light image that are obtained as a result of imaging.

According to the first embodiment of the present disclosure, there is provided an imaging method of an imaging apparatus, the imaging apparatus including an unpolarized light-emitting portion configured to emit light having an unpolarized component, a polarized light-emitting portion configured to emit light having a predetermined polarized component through the first polarization filter, and an imaging element configured to image a subject, which is irradiated with light by one of the unpolarized light-emitting portion and the polarized light-emitting portion, through a second polarization filter, the first polarization filter and the second polarization filter having polarization directions in an orthogonal relationship to each other, the method including by the imaging apparatus: imaging the subject irradiated with light by the unpolarized light-emitting portion and the subject irradiated with light by the polarized light-emitting portion in a time division manner; and outputting an unpolarized light image and an orthogonal polarized light image.

In the first embodiment of the present disclosure, in the imaging apparatus, the subject irradiated with light by the unpolarized light-emitting portion and the subject irradiated with light by the polarized light-emitting portion are imaged in the time division manner and the unpolarized light image and the orthogonal polarized light image are output.

According to a second embodiment of the present disclosure, there is provided an image processing apparatus including a specular reflection image generator configured to acquire an unpolarized light image and an orthogonal polarized light image that are captured by an imaging apparatus including an unpolarized light-emitting portion configured to emit light having an unpolarized component, a polarized light-emitting portion configured to emit light having a predetermined polarized component through the first polarization filter, and an imaging element configured to image a subject, which is irradiated with light by one of the unpolarized light-emitting portion and the polarized light-emitting portion, through a second polarization filter, the first polarization filter and the second polarization filter having polarization directions in an orthogonal relationship to each other, and generate, from the unpolarized light image and the orthogonal polarized light image, a specular reflection image being an image having a specular reflection component.

According to the second embodiment of the present disclosure, there is provided an imaging processing method of an image processing apparatus, including: acquiring an unpolarized light image and an orthogonal polarized light image that are captured by an imaging apparatus including an unpolarized light-emitting portion configured to emit light having an unpolarized component, a polarized light-emitting portion configured to emit light having a predetermined polarized component through the first polarization filter, and an imaging element configured to image a subject, which is irradiated with light by one of the unpolarized light-emitting portion and the polarized light-emitting portion, through a second polarization filter, the first polarization filter and the second polarization filter having polarization directions in an orthogonal relationship to each other; and generating a specular reflection image being an image having a specular reflection component from the unpolarized light image and the orthogonal polarized light image.

According to the second embodiment of the present disclosure, there is provided a program that causes a computer to execute a process, the computer being configured to process an unpolarized light image and an orthogonal polarized light image that are captured by an imaging apparatus including an unpolarized light-emitting portion configured to emit light having an unpolarized component, a polarized light-emitting portion configured to emit light having a predetermined polarized component through the first polarization filter, and an imaging element configured to image a subject, which is irradiated with light by one of the unpolarized light-emitting portion and the polarized light-emitting portion, through a second polarization filter, the first polarization filter and the second polarization filter having polarization directions in an orthogonal relationship to each other, the process including generating a specular reflection image being an image having a specular reflection component from the unpolarized light image and the orthogonal polarized light image.

In the second embodiment of the present disclosure, the specular reflection image being the image having the specular reflection component is generated from the unpolarized light image and the orthogonal polarized light image.

According to a third embodiment of the present disclosure, there is provided an image processing apparatus including a parallel polarized light image generator configured to acquire an unpolarized light image and an orthogonal polarized light image that are captured by an imaging apparatus including an unpolarized light-emitting portion configured to emit light having an unpolarized component, a polarized light-emitting portion configured to emit light having a predetermined polarized component through the first polarization filter, and an imaging element configured to image a subject, which is irradiated with light by one of the unpolarized light-emitting portion and the polarized light-emitting portion, through a second polarization filter, the first polarization filter and the second polarization filter having polarization directions in an orthogonal relationship to each other, and generate a parallel polarized light image being an image having a parallel polarized component from the unpolarized light image and the orthogonal polarized light image.

According to the third embodiment of the present disclosure, there is provided an imaging processing method of an image processing apparatus including: acquiring an unpolarized light image and an orthogonal polarized light image that are captured by an imaging apparatus including an unpolarized light-emitting portion configured to emit light having an unpolarized component, a polarized light-emitting portion configured to emit light having a predetermined polarized component through the first polarization filter, and an imaging element configured to image a subject, which is irradiated with light by one of the unpolarized light-emitting portion and the polarized light-emitting portion, through a second polarization filter, the first polarization filter and the second polarization filter having polarization directions in an orthogonal relationship to each other; and generating a parallel polarized light image being an image having a parallel polarized component from the unpolarized light image and the orthogonal polarized light image.

According to the third embodiment of the present disclosure, there is provided a program that causes a computer to execute a process, the computer being configured to process an unpolarized light image and an orthogonal polarized light image that are captured by an imaging apparatus including an unpolarized light-emitting portion configured to emit light having an unpolarized component, a polarized light-emitting portion configured to emit light having a predetermined polarized component through the first polarization filter, and an imaging element configured to image a subject, which is irradiated with light by one of the unpolarized light-emitting portion and the polarized light-emitting portion, through a second polarization filter, the first polarization filter and the second polarization filter having polarization directions in an orthogonal relationship to each other, the process including generating a parallel polarized light image being an image having a parallel polarized component from the unpolarized light image and the orthogonal polarized light image.

In the third embodiment of the present disclosure, the parallel polarized light image being the image having the parallel polarized component is generated from the unpolarized light image and the orthogonal polarized light image.

Note that the program may be provided by being transmitted through a transmission medium or recorded in a recording medium.

The imaging apparatus and the image processing apparatus may be independent apparatuses or may be internal blocks constituting a single apparatus.

According to the first to third embodiments of the present disclosure, it is possible to evaluate a skin surface condition with a lower-cost configuration.

Note that the effect above is not necessarily limited and may be any of effects set forth in the present disclosure.

These and other objects, features and advantages of the present disclosure will become more apparent in light of the following detailed description of best mode embodiments thereof, as illustrated in the accompanying drawings.

DETAILED DESCRIPTION OF EMBODIMENTS

Hereinafter, embodiments for carrying out the present disclosure (hereinafter, referred to as embodiments) will be described with reference to the drawings. Note that descriptions thereof will be made in the following order.

1. First Embodiment (Imaging System That Evaluates Skin Shine)
2. Second Embodiment (Imaging System That Evaluates Skin Texture)
3. Third Embodiment (Imaging System That Evaluates Skin Shine and Texture)
4. Fourth Embodiment (Imaging System That Performs Image Processing at Server)

1. First Embodiment

<Block Diagram of Imaging System>

Figure 1:
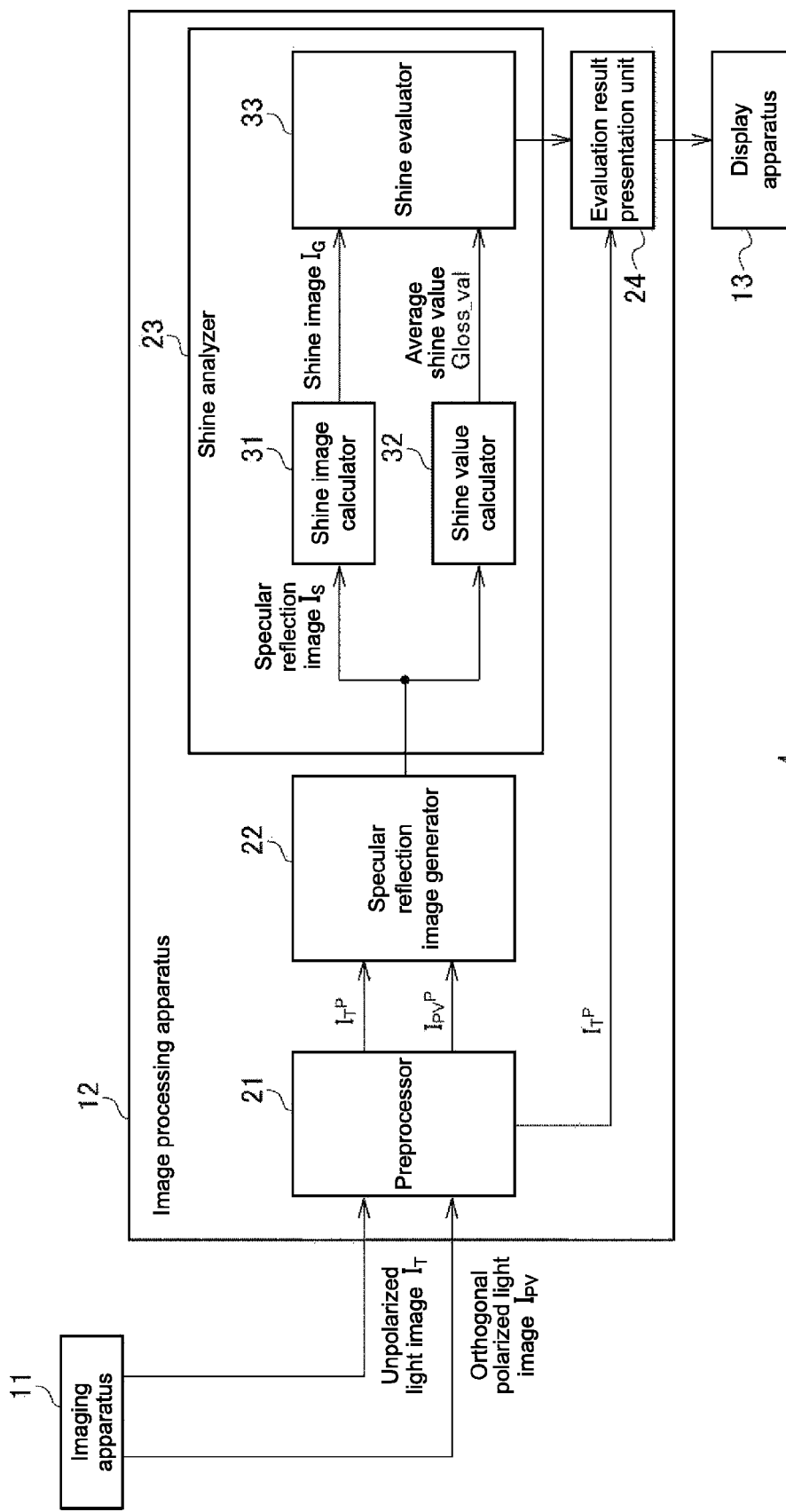
FIG. 1 is a block diagram showing an imaging system according to a first embodiment of the present disclosure.

FIG. 1 is a block diagram showing an imaging system according to a first embodiment of the present disclosure.

An imaging system 1 shown in FIG. 1 includes an imaging apparatus 11, an image processing apparatus 12, and a display apparatus 13. The imaging system 1 is a system that captures a skin image and evaluates skin shine as a skin surface condition.

The imaging apparatus 11 captures a skin image of an examinee and supplies the captured skin image to the image processing apparatus 12. More specifically, the imaging apparatus 11 captures, as the skin image, two kinds of (two) images of an unpolarized light image $I_T$ and an orthogonal polarized light image $I_{PV}$, and supplies them to the image processing apparatus 12.

Figure 2:
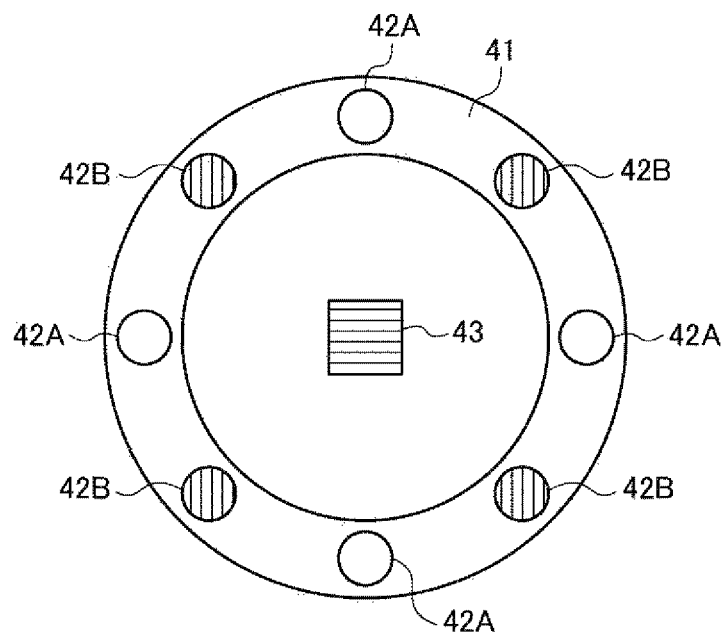
FIG. 2 is a view showing a lens-barrel portion of an imaging apparatus.

FIG. 2 is a view showing a lens-barrel portion of the imaging apparatus 11.

A lens-barrel 41 of the imaging apparatus 11 includes a plurality of light-emitting portions 42 in an annular form. The lens-barrel 41 includes an image sensor 43 at a center thereof. The image sensor 43 is configured by an imaging element, for example, a complementary metal oxide semiconductor (CMOS) image sensor or a charge coupled device (CCD). The image sensor 43 is, at a front surface thereof, provided with a polarization filter.

The light-emitting portions 42 include unpolarized light-emitting portions 42A and polarized light-emitting portions 42B. The unpolarized light-emitting portions 42A emit light having an unpolarized component to the skin of the examinee. The polarized light-emitting portions 42B emit light having a predetermined polarized component to the skin of the examinee. Each of the unpolarized light-emitting portions 42A includes a light-emitting diode (LED) light source that emits white light.

On the other hand, each of the polarized light-emitting portions 42B includes an LED light source that emits white light and a polarization filter provided at a front surface thereof. The polarization filter of the polarized light-emitting portions 42B and the polarization filter of the image sensor 43 are attached such that polarization directions thereof are orthogonal to each other.

The unpolarized light-emitting portions 42A and the polarized light-emitting portions 42B are arranged in a point symmetrical manner with respect to the image sensor 43 as shown in FIG. 2.

Although the four unpolarized light-emitting portions 42A and the four polarized light-emitting portions 42B are provided in the example of FIG. 2, the number of unpolarized light-emitting portions 42A and polarized light-emitting portions 42B is not limited thereto. At least two unpolarized light-emitting portions 42A and two polarized light-emitting portions 42B only need to be provided in a point symmetrical manner. Alternatively, six unpolarized light-emitting portions 42A and six polarized light-emitting portions 42B may be provided in a point symmetrical manner.

Note that, in order to eliminate luminance non-uniformity, it is desirable to provide the unpolarized light-emitting portions 42A and the polarized light-emitting portions 42B in a point symmetrical manner and set the number of unpolarized light-emitting portions 42A and the number of polarized light-emitting portions 42B to be equal. However, other arrangements are possible.

First, by the image sensor 43 imaging the skin of the examinee via the polarization filter of a first polarization direction (horizontal direction) in a state in which the skin of the examinee serving as a subject is irradiated with light by the unpolarized light-emitting portions 42A, the imaging apparatus 11 generates an unpolarized light image $I_T$ of the skin of the examinee. Then, the imaging apparatus 11 supplies the unpolarized light image $I_T$ to the image processing apparatus 12.

Next, by the image sensor 43 imaging the skin of the examinee in a state in which the skin being irradiated with light by the polarized light-emitting portions 42B via the polarization filter of a second polarization direction (vertical direction), the imaging apparatus 11 generates an orthogonal polarized light image $I_{PV}$ of the skin of the examinee. Then, the imaging apparatus 11 supplies the orthogonal polarized light image $I_{PV}$ to the image processing apparatus 12.

Thus, in comparison with the case where three (three kinds of) polarization filters are prepared, two of the three polarization filters are placed on the light source side such that two kinds of polarizations of the parallel polarization and the orthogonal polarization can be provided, and one of the three polarization filters is placed on the image sensor side, only two kinds of polarization filters are necessary.

In addition, in comparison with the case where two (two kinds of) polarization filters are prepared, the polarization filters are placed on the light source side and the image sensor side, respectively, and imaging is performed with either the light source or the image sensor being rotated at 90 degrees, the rotation function can be omitted.

Thus, according to the present technology, skin images necessary for evaluating a skin surface condition with a lower-cost configuration can be acquired, and hence it is possible to evaluate the skin surface condition with the low-cost configuration.

Note that the order of imaging by the unpolarized light-emitting portions 42A and imaging by the polarized light-emitting portions 42B may be opposite. Thus, the imaging apparatus 11 only needs to be able to perform imaging by the unpolarized light-emitting portions 42A and imaging by the polarized light-emitting portions 42B in a time division manner, to thereby generate an unpolarized light image $I_T$ and an orthogonal polarized light image $I_{PV}$.

As long as the first polarization direction and the second polarization direction are in an orthogonal relationship to each other, the polarization directions of the image sensor 43 and the polarized light-emitting portions 42B are not limited.

Referring back to FIG. 1, the image processing apparatus 12 includes a preprocessor 21, a specular reflection image generator 22, a shine analyzer 23, and an evaluation result presentation unit 24. The shine analyzer 23 includes a shine image calculator 31, a shine value calculator 32, and a shine evaluator 33.

The preprocessor 21 is supplied with two (two kinds of) skin images captured by the imaging apparatus 11, that is, the unpolarized light image $I_T$ and the orthogonal polarized light image $I_{PV}$ from the imaging apparatus 11.

The preprocessor 21 performs preprocessing for making it easy to perform processing at the subsequent stages on the unpolarized light image $I_T$ and the orthogonal polarized light image $I_{PV}$ supplied from the imaging apparatus 11. Specifically, the preprocessor 21 adjusts luminance levels of the two images to an optimal luminance level (average luminance).

<Outline of Preprocessor 21>

Figure 3:
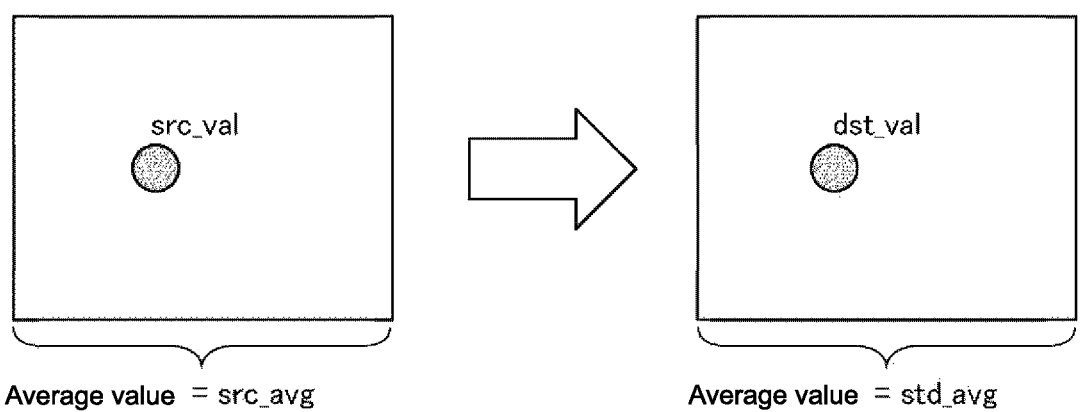
FIG. 3 is a view showing an outline of preprocessing by a preprocessor.

FIG. 3 is a view showing an outline of preprocessing by the preprocessor 21.

Assuming that an average value of luminance values of the acquired image is indicated by src_avg and a desired level as an average luminance of the image is indicated by a standard value std_val, the preprocessor 21 adjusts the luminance value src_val of a predetermined pixel of the image before the adjustment to a luminance value dst_val of the image after the adjustment according to the following expression.

$$dst\_val = src\_val + (std\_val - src\_avg)$$

More specifically, the preprocessor 21 calculates a luminance value $I_T^P(x, y)$ after the adjustment based on a luminance value $I_T^P(x, y)$ before the adjustment of a pixel (x, y) of the unpolarized light image $I_T$ according to the following Expression (1).

$$I_T^P(x, y) = I_T(x, y) + \left(std\_val - \frac{\sum_{x,y} I_T(x, y)}{N}\right) \quad (1)$$

Further, the preprocessor 21 calculates a luminance value $I_{PV}^P(x, y)$ after the adjustment based on a luminance value $I_{PV}$ (x, y) before the adjustment of the pixel (x, y) of the orthogonal polarized light image $I_{PV}$ according to the following Expression (2).

$$I_{PV}^P(x, y) = I_{PV}(x, y) + \left(std\_val - \frac{\sum_{x,y} I_{PV}(x, y)}{N}\right) \quad (2)$$

N being a denominator of the fraction in each of Expressions (1) and (2) indicates the number of pixels of the unpolarized light image $I_T$ or the orthogonal polarized light image $I_{PV}$. Note that the standard value std_val is set and input as a fixed value in advance.

The preprocessor 21 supplies the unpolarized light image $I_T^P$ and the orthogonal polarized light image $I_{PV}^P$ after preprocessing to the specular reflection image generator 22. Further, the preprocessor 21 supplies the unpolarized light image $I_T^P$ after preprocessing also to the evaluation result presentation unit 24.

Using the unpolarized light image $I_T^P$ and the orthogonal polarized light image $I_{PV}^P$ after preprocessing that are supplied from the preprocessor 21, the specular reflection image generator 22 generates a specular reflection image $I_S$ being an image having a specular reflection component. Then, the specular reflection image generator 22 supplies the specular reflection image $I_S$ to the shine image calculator 31 and the shine value calculator 32.

<Configuration of Specular Reflection Image Generator 22>

Figure 4:
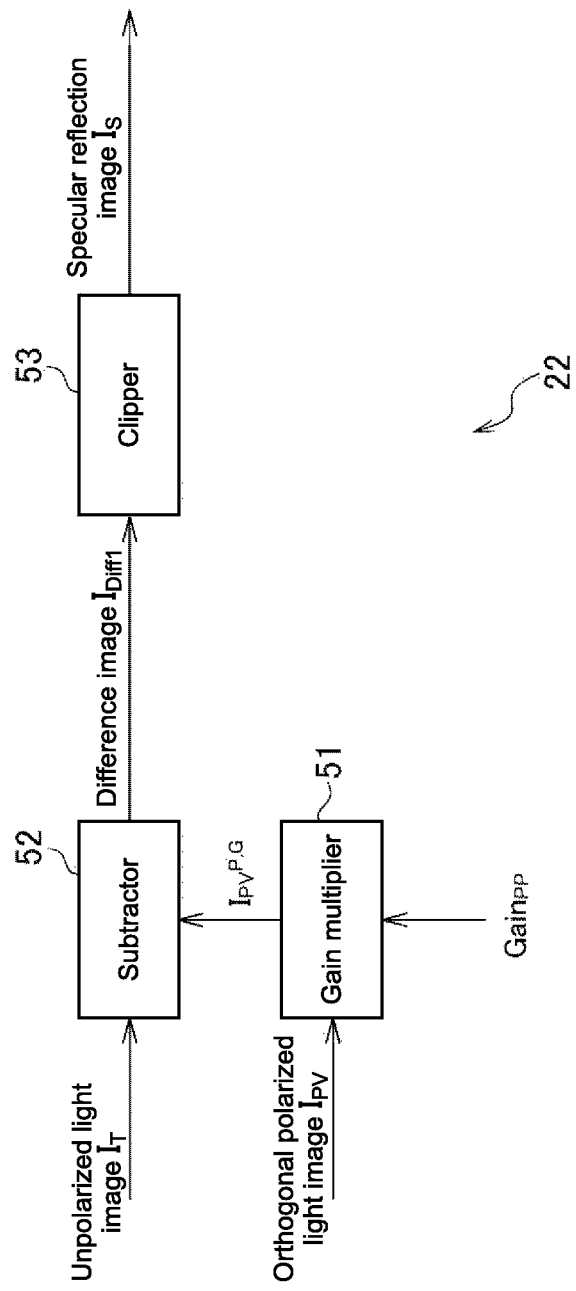
FIG. 4 is a block diagram showing a detailed configuration example of a specular reflection image generator.

FIG. 4 is a block diagram showing a detailed configuration example of the specular reflection image generator 22.

The specular reflection image generator 22 includes a gain multiplier 51, a subtractor 52, and a clipper 53.

The gain multiplier 51 multiplies a gain $Gain_{PP}$ with the orthogonal polarized light image $I_{PV}^P$ according to the following Expression (3) and obtains an orthogonal polarized light image $I_{PV}^{P,G}$ after the gain multiplication.

$$I_{PV}^{P,G}(x,y) = Gain_{PP} \cdot I_{PV}^P(x,y) \quad (3)$$

Here, a value for making the average luminance of the unpolarized light image $I_T$ equal to the average luminance of the orthogonal polarized light image $I_{PV}$ is set as the gain $Gain_{PP}$. However, in this embodiment, the average luminances of the two images are already adjusted by the preprocessor 21 to the same value, and hence $Gain_{PP}=1.0$ can be set.

In other words, the preprocessor 21 may be omitted. In this case, the gain $Gain_{PP}$ for making the average luminance of the unpolarized light image $I_T$ equal to the average luminance of the orthogonal polarized light image $I_{PV}$ is calculated by another block or input from an external device and multiplied with respect to the orthogonal polarized light image $I_{PV}^P$ according to Expression (3). Alternatively, a value calculated according to Expression (6) in a second embodiment to be described later may be employed as the gain Gainpp.

The subtractor 52 subtracts from the unpolarized light image $I_T^P$ the orthogonal polarized light image $I_{PV}^{P,\,G}$ after the gain multiplication and generates a difference image $I_{Diff1}$. Specifically, the subtractor 52 performs a calculation according to the following Expression (4) on each pixel of the unpolarized light image $I_T^P$.

$$I_{Diff1}(x,y) = I_T^P(x,y) - I_{PV}^{P,G}(x,y) \quad (4)$$

According to Expression (4), a fluctuating component of the images, for example, a minute structure of a surface or a specular reflection component can be extracted.

The clipper 53 performs clipping processing of clipping the difference image $I_{Diff1}$ calculated by the subtractor 52 such that the image is in an appropriate range. Then, the clipper 53 outputs the image after clipping processing as the specular reflection image $I_S$.

Figure 5:
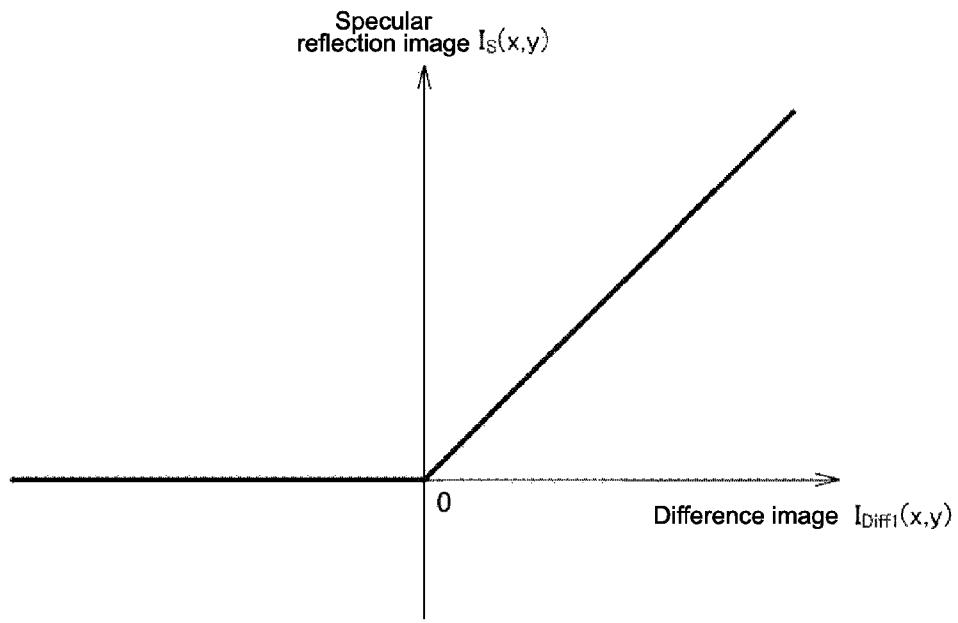
FIG. 5 is a view explaining the processing contents of clipping processing by a clipper.

FIG. 5 shows a conversion graph indicating processing contents of clipping processing by the clipper 53. In FIG. 5, a horizontal axis indicates the luminance value $I_{Diff1}$ (x, y) of the pixel (x, y) of the difference image $I_{Diff1}$ and a vertical axis indicates the luminance value $I_S$ (x, y) of the specular reflection image $I_S$ after clipping processing.

As shown in FIG. 5, the clipper 53 performs processing of setting a negative luminance value generated by the difference calculation of the subtractor 52 to 0.

As described above, the specular reflection image generator 22 calculates the specular reflection image $I_S$, using the unpolarized light image $I_T^P$ and the orthogonal polarized light image $I_{PV}^P$ after preprocessing that are supplied from the preprocessor 21. Then, the specular reflection image generator 22 supplies the specular reflection image $I_S$ to the shine image calculator 31 and the shine value calculator 32.

<Configuration of Shine Analyzer 23>

Referring back to FIG. 1, the shine analyzer 23 analyzes the skin shine, using the specular reflection image $I_S$ supplied from the specular reflection image generator 22.

The shine image calculator 31 calculates a shine image $I_G$ based on the specular reflection image $I_S$ supplied from the specular reflection image generator 22. The shine image $I_G$ is an image indicating an amount of sebum of the examinee.

Figure 6:
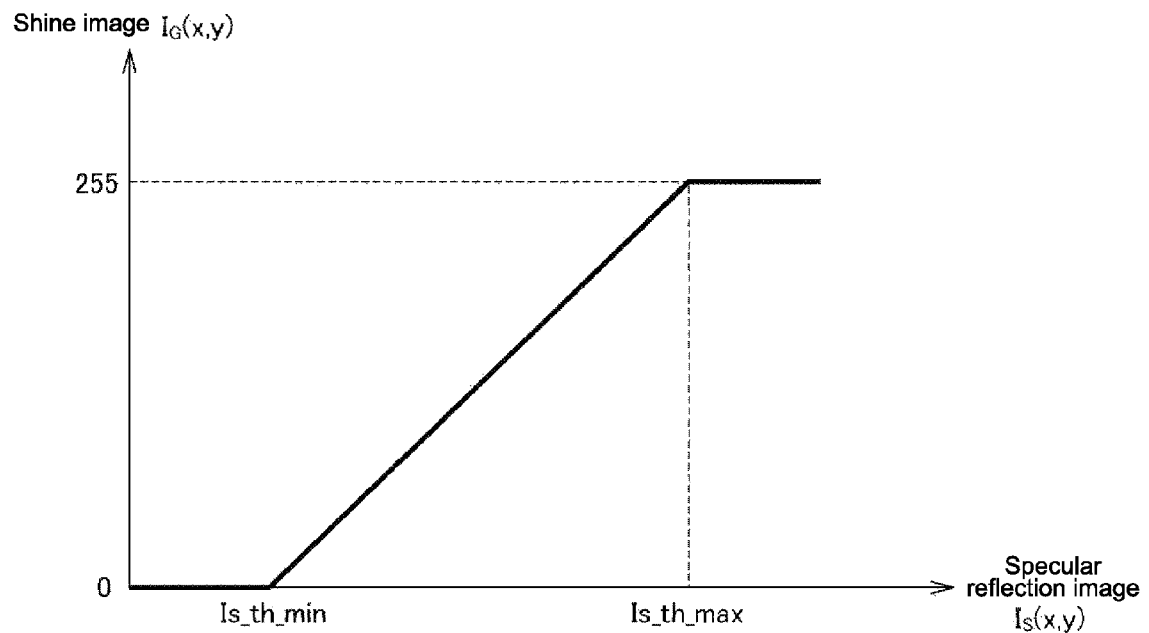
FIG. 6 is a view explaining the contents of processing by a shine image calculator.

FIG. 6 is a view showing the contents of processing by the shine image calculator 31 with respect to the luminance value $I_S$ (x, y) of the pixel (x, y) of the specular reflection image $I_S$. In FIG. 6, a horizontal axis indicates the luminance value $I_S$ (x, y) of the pixel (x, y) of the specular reflection image $I_S$ and a vertical axis indicates the luminance value $I_G$ (x, y) of the pixel (x, y) of the shine image $I_G$.

As shown in FIG. 6, the shine image calculator 31 calculates the shine image $I_G$ by mapping a range of from the luminance value Is_th_min to the luminance value Is_th_max of the specular reflection image $I_S$ to luminance values of from 0 to 255.

Referring back to FIG. 1, the shine value calculator 32 calculates a shine value (amount of sebum) Gloss_val based on the specular reflection image $I_S$ supplied from the specular reflection image generator 22. The shine value Gloss_val is calculated according to the following Expression (5).

$$\text{Gloss\_val} = \frac{\sum_{x,y} I_S(x, y)}{N} \quad (5)$$

In Expression (5), N of a denominator indicates the number of pixels of the specular reflection image $I_S$. Thus, the shine value Gloss_val can be calculated based on the average luminance of the specular reflection image $I_S$.

The shine image $I_G$ calculated by the shine image calculator 31 and the shine value Gloss_val calculated by the shine value calculator 32 are supplied to the shine evaluator 33.

The shine evaluator 33 calculates a shine evaluation value Gloss_eval from the shine value Gloss_val calculated by the shine value calculator 32, using a shine evaluation value calculation graph stored therein.

Figure 7:
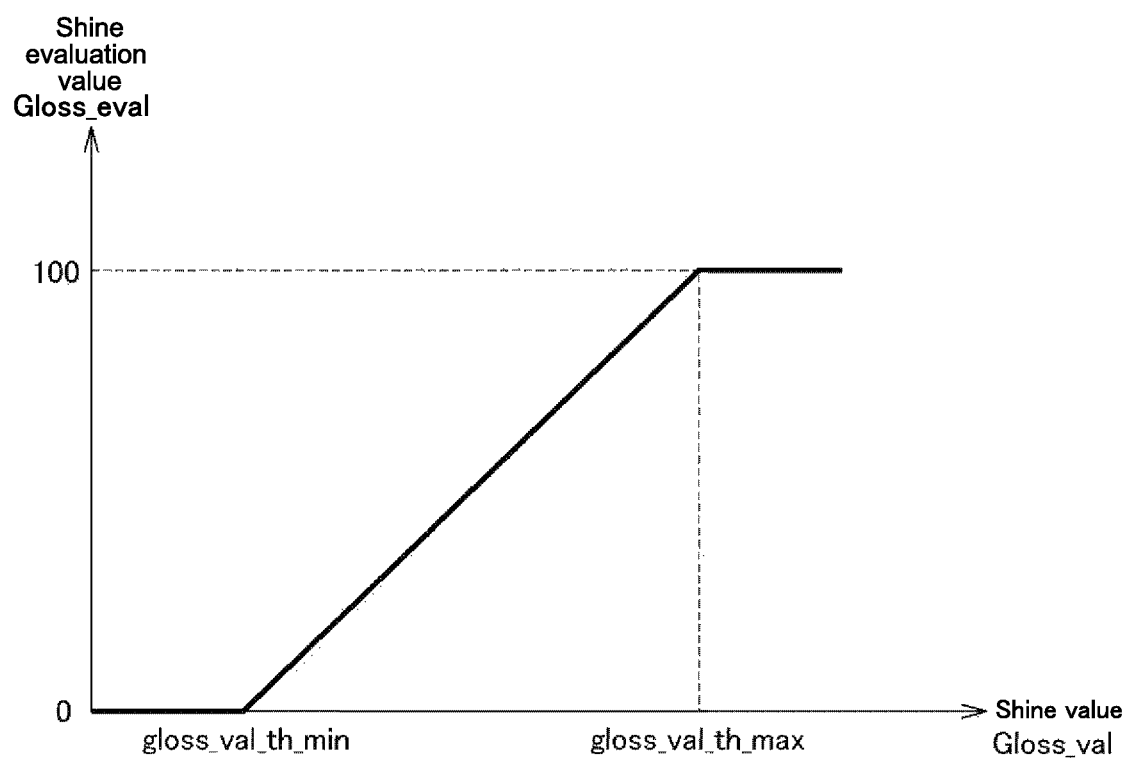
FIG. 7 is a view showing an example of a shine evaluation value calculation graph stored in a shine evaluator.

FIG. 7 shows an example of the shine evaluation value calculation graph stored in the shine evaluator 33.

The shine evaluation value calculation graph is, for example, as shown in FIG. 7, a graph that assigns 0 as the shine evaluation value Gloss_eval to a shine value Gloss_val smaller than a first value gloss_val_th_min, assigns a shine evaluation value Gloss_eval of from 0 to 100 to a shine value Gloss_val equal to or larger than the first value gloss_val_th_min and equal to or smaller than a second value gloss_val_th_max, and assigns a shine evaluation value Gloss_eval of 100 to a shine value Gloss_val larger than the second value gloss_val_th_max. With this, the shine value Gloss_val is converted into the shine evaluation value Gloss_eval taking any value of from 0 to 100. Note that the shine evaluation value calculation graph is not limited to the example of FIG. 7.

The shine evaluator 33 supplies the shine evaluation value Gloss_eval calculated based on the shine evaluation value calculation graph to the evaluation result presentation unit 24 together with the shine image $I_G$ supplied from the shine image calculator 31.

The evaluation result presentation unit 24 causes the display apparatus 13 to display information indicating an evaluation result of the skin shine of the examinee, using the unpolarized light image $I_T^P$ after preprocessing that is supplied from the preprocessor 21 and the shine evaluation value Gloss_eval and the shine image $I_G$ that are supplied from the shine evaluator 33.

The display apparatus 13 includes a liquid crystal display (LCD), an organic electro luminescence (EL) display, and the like. The display apparatus 13 displays a predetermined image based on an image signal supplied from the evaluation result presentation unit 24.

Note that the display apparatus 13 may be included as a part of the image processing apparatus 12 or may be an apparatus having a function other than the display function, for example, a portable information terminal such as a cellular phone or a television receiver. In other words, any types of apparatuses having at least the display function may be used as the display apparatus 13.

<Example of Evaluation Result Presentation Screen>

Figure 8:
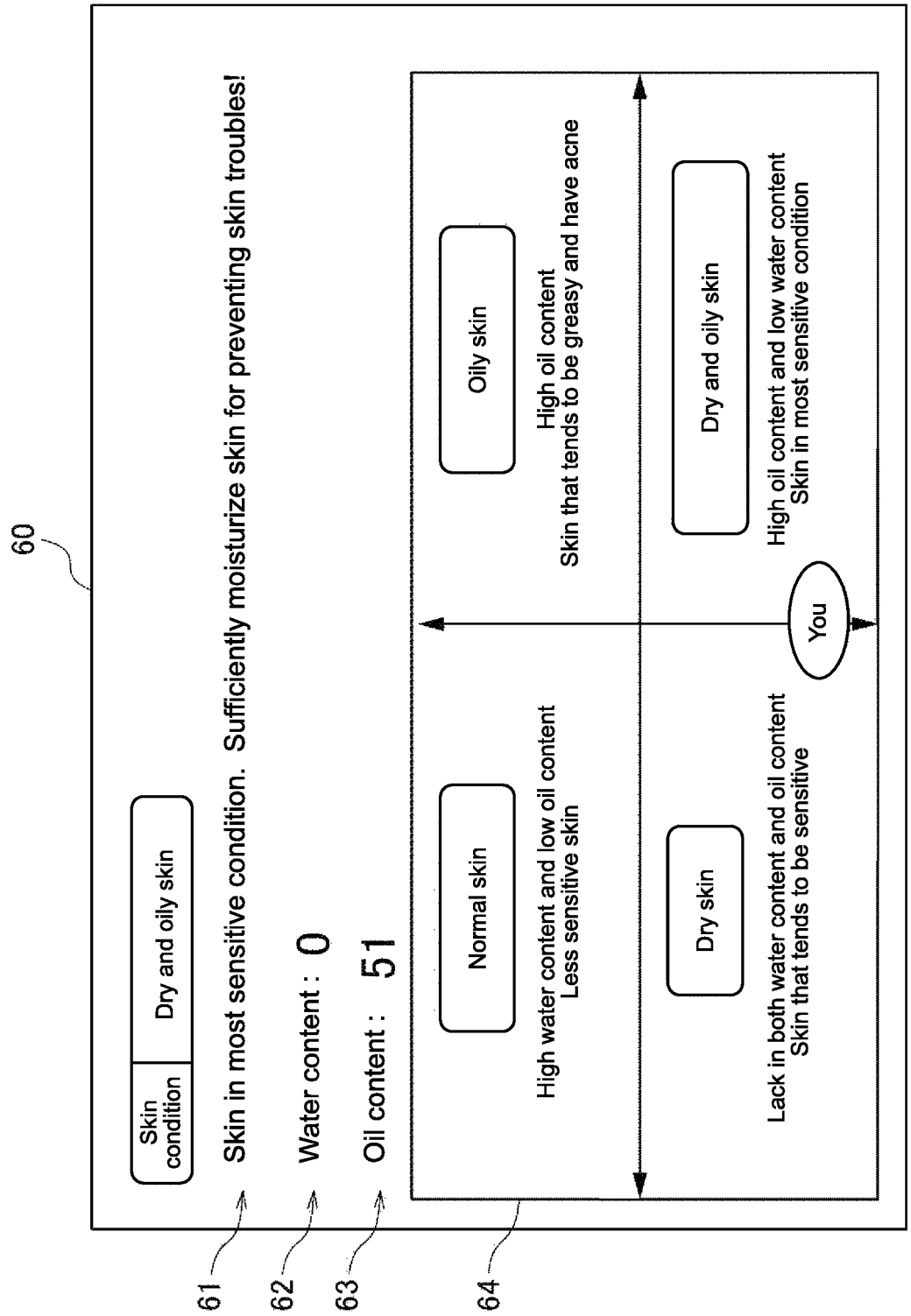
FIG. 8 is a view showing an example of an evaluation result presentation screen.
Figure 9:
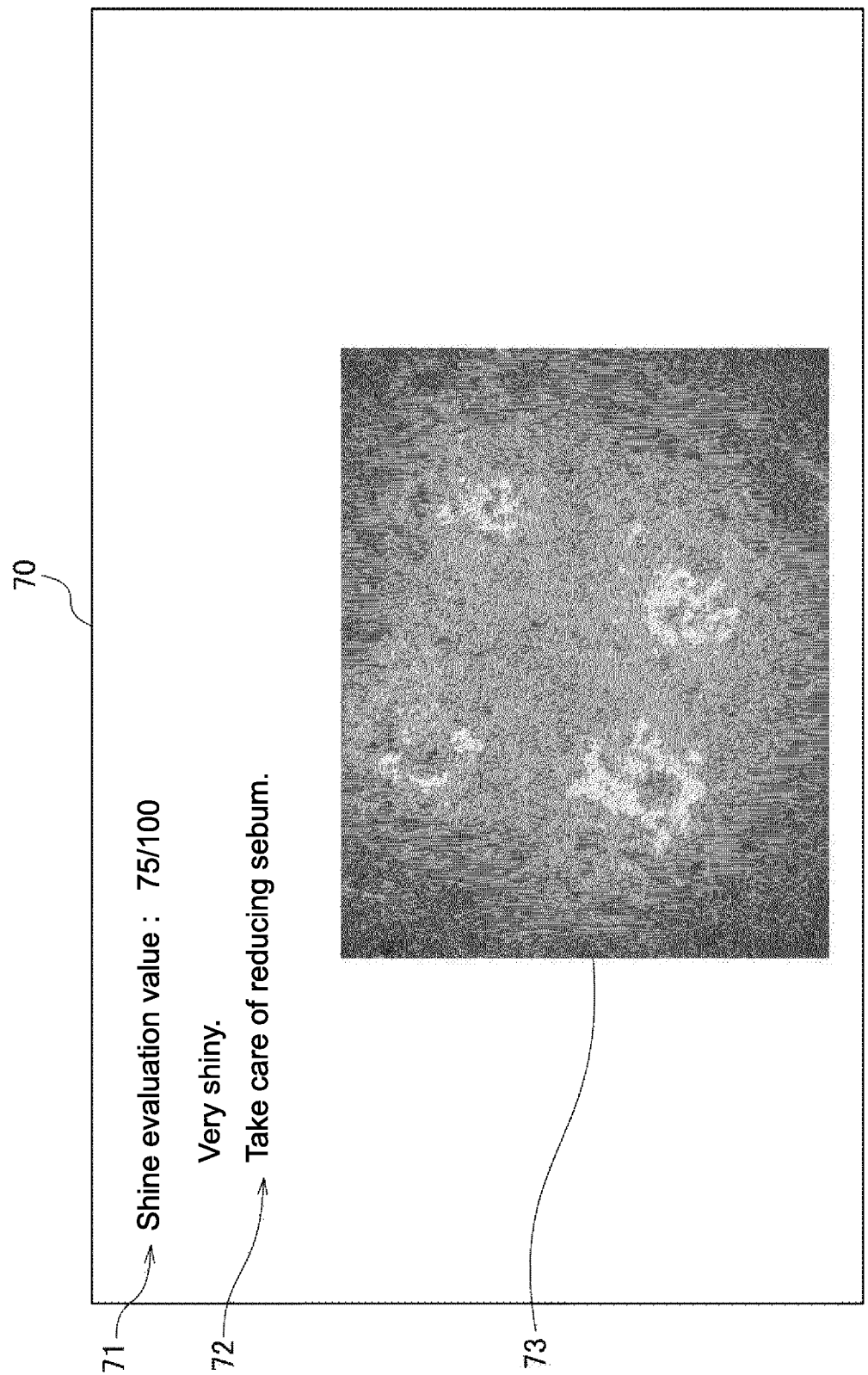
FIG. 9 is a view showing another example of the evaluation result presentation screen.

Referring to FIGS. 8 and 9, an example of the evaluation result presentation screen displayed by the evaluation result presentation unit 24 on the display apparatus 13 will be described.

FIG. 8 shows an example of the evaluation result presentation screen that presents the evaluation result of the skin shine of the examinee using the shine evaluation value Gloss_eval.

An evaluation result presentation screen 60 shown in FIG. 8 includes a message presentation portion 61, a water content presentation portion 62, a oil content presentation portion 63, and a skin condition map presentation portion 64.

In the message presentation portion 61, a predetermined message selected from among a plurality of messages, which are prepared in advance, based on the oil content and the water content of the examinee is shown. In the example of FIG. 8, a message saying "Skin in most sensitive condition. Sufficiently moisturize skin for preventing skin troubles!" is shown.

In the water content presentation portion 62, a measurement result of the water content of the examinee is shown. The water content of the examinee is measured by, for example, a water content measuring instrument (measurement unit) that measures the water content of the skin in an electrostatic capacitance manner. The measured water content is supplied to the evaluation result presentation unit 24. In the example of FIG. 8, "0" is shown as the water content.

In the oil content presentation portion 63, a measurement result of the oil content of the examinee is shown. The shine evaluation value Gloss_eval supplied from the shine evaluator 33 is shown in the oil content presentation portion 63 as the oil content of the examinee. In the example of FIG. 8, "51" is shown as the oil content.

In the skin condition map presentation portion 64, the oil content and the water content of the examinee are shown in a two-dimensional map indicating the oil content on a horizontal axis and the water content on a vertical axis. The skin condition is classified into "normal skin," "oily skin," "oily and dry skin," and "dry skin" respectively corresponding to quadrants of the two-dimensional map. Specifically, the skin condition is considered as "dry skin" when the water content is smaller than 50 and the oil content is smaller than 50, as "oily and dry skin" when the water content is smaller than 50 and the oil content is equal to or larger than 50, as "normal skin" when the water content is equal to or larger than 50 and the oil content is smaller than 50, and as "oily skin" when the water content is equal to or larger than 50 and the oil content is equal to or larger than 50. At a point corresponding to the oil content and the water content of the examinee in the two-dimensional map, a word "You" indicating the skin condition of the examinee is shown.

FIG. 9 shows another example of the evaluation result presentation screen that presents the evaluation result of the skin shine of the examinee.

An evaluation result presentation screen 70 shown in FIG. 9 includes a shine evaluation value presentation portion 71, a message presentation portion 72, and a skin image presentation portion 73.

In the shine evaluation value presentation portion 71, the shine evaluation value Gloss_eval supplied from the shine evaluator 33 is shown. FIG. 9 is an example in the case where the shine evaluation value Gloss_eval supplied from the shine evaluator 33 is 75, "Shine evaluation value: 75/100" is shown in the shine evaluation value presentation portion 71.

In the message presentation portion 72, a predetermined message selected from among a plurality of messages, which are prepared in advance, based on the shine evaluation value Gloss_eval of the examinee is shown. In the example of FIG. 9, a message saying "Very shiny. Take care of reducing sebum." is shown.

In the skin image presentation portion 73, an image overlapping the shine image $I_G$ supplied from the shine evaluator 33 on the unpolarized light image $I_T^P$ after preprocessing that is supplied from the preprocessor 21 is shown. The shine image $I_G$ has a higher luminance in a shinier region. Thus, the examinee can easily check the skin surface condition.

<Skin Shine Evaluation Processing>

Figure 10:
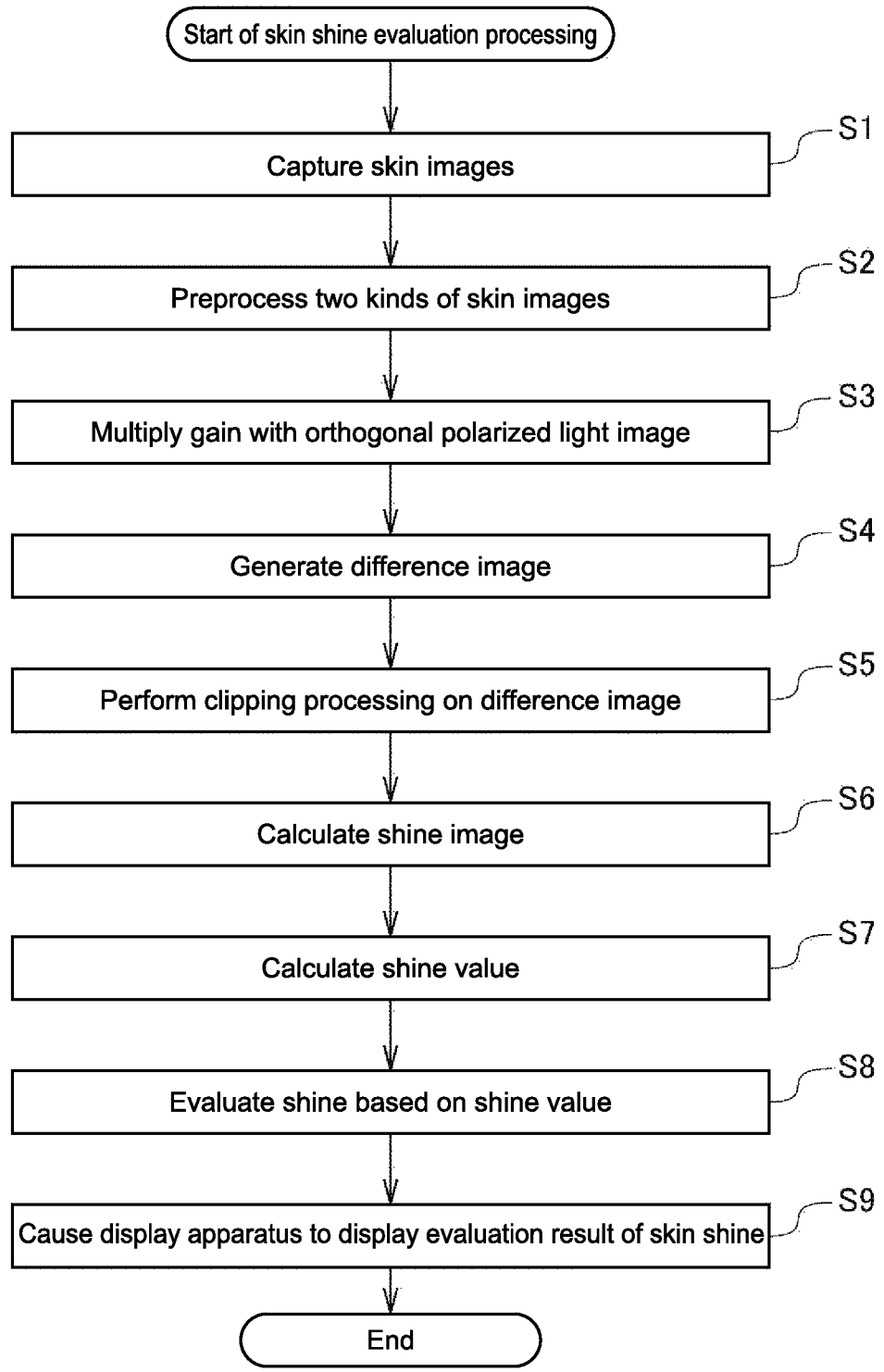
FIG. 10 is a flowchart explaining skin shine evaluation processing in the imaging system according to the first embodiment.

Next, referring to a flowchart in FIG. 10, skin shine evaluation processing in the imaging system 1 according to the first embodiment will be described.

First, in Step S1, the imaging apparatus 11 captures skin images. Specifically, the imaging apparatus 11 generates two kinds of (two) images of the unpolarized light image $I_T$ and the orthogonal polarized light image $I_{PV}$ by imaging the skin of the examinee while emitting light to the unpolarized light-emitting portions 42A and the polarized light-emitting portions 42B in a time division manner. The imaging apparatus 11 supplies the resulting captured images to the image processing apparatus 12.

In Step S2, the preprocessor 21 performs preprocessing for making it easy to perform processing at the subsequent stages on the unpolarized light image $I_T$ and the orthogonal polarized light image $I_{PV}$ that are supplied from the imaging apparatus 11. Specifically, the preprocessor 21 adjusts luminance values according to Expressions (1) and (2) such that the average luminance of the images take an optimal value. The unpolarized light image $I_T^P$ and the orthogonal polarized light image $I_{PV}^P$ after preprocessing are supplied to the specular reflection image generator 22. The unpolarized light image $I_T^P$ after preprocessing is also supplied to the evaluation result presentation unit 24.

In Step S3, the gain multiplier 51 of the specular reflection image generator 22 multiplies the gain $Gain_{PP}$ with the orthogonal polarized light image $I_{PV}^P$ according to Expression (3) above. The orthogonal polarized light image $I_{PV}^{P, G}$ after the gain multiplication is supplied to the subtractor 52.

In Step S4, the subtractor 52 generates a difference image $I_{Diff1}$ by subtracting from the orthogonal polarized light image $I_{PV}$ the orthogonal polarized light image $I_{PV}^{P, G}$ after the gain multiplication. Specifically, the subtractor 52 performs the calculation of Expression (4) above for each of pixels of the orthogonal polarized light image $I_{PV}$.

In Step S5, the clipper 53 performs clipping processing of clipping the difference image $I_{Diff1}$ calculated by the subtractor 52 such that the image is included in an appropriate range. Then, the clipper 53 outputs the image after clipping processing to the shine image calculator 31 and the shine value calculator 32 as the specular reflection image $I_S$.

In Step S6, the shine image calculator 31 of the shine analyzer 23 calculates the shine image $I_G$ based on the specular reflection image $I_S$ supplied from the specular reflection image generator 22. More specifically, as shown in FIG. 6, the shine image calculator 31 calculates the shine image $I_G$ by mapping a range of from the luminance value Is_th_min to the luminance value Is_th_max of the specular reflection image $I_S$ to the luminance values of from 0 to 255.

In Step S7, the shine value calculator 32 of the shine analyzer 23 calculates the shine value Gloss_val according to Expression (5) above based on the specular reflection image $I_S$ supplied from the specular reflection image generator 22.

In Step S8, the shine evaluator 33 of the shine analyzer 23 evaluates the shine based on the shine value Gloss_val calculated by the shine image calculator 31. Specifically, using the shine evaluation value calculation graph shown in FIG. 7, the shine evaluator 33 calculates the shine evaluation value Gloss_eval based on the shine value Gloss_val. The calculated shine evaluation value Gloss_eval is supplied from the shine evaluator 33 to the evaluation result presentation unit 24 together with the shine image $I_G$ supplied from the shine image calculator 31.

In Step S9, the evaluation result presentation unit 24 causes the display apparatus 13 to display the evaluation result of the skin shine of the examinee. More specifically, the evaluation result presentation unit 24 causes the display apparatus 13 to display the evaluation result presentation screen shown in FIG. 8 and the evaluation result presentation screen shown in FIG. 9, using the unpolarized light image $I_T^P$ after preprocessing that is supplied from the preprocessor 21, the shine evaluation value Gloss_eval and the shine image $I_G$ that are supplied from the shine evaluator 33, and the like.

In this manner, skin shine evaluation processing is completed.

By skin shine evaluation processing described above, the skin surface condition can be evaluated using the unpolarized light image $I_T$ and the orthogonal polarized light image $I_{PV}$ that are obtained by the imaging apparatus 11, and hence it is possible to evaluate the skin surface condition with the low-cost configuration.

According to the above-mentioned first embodiment, the shine value is evaluated without binarizing the unpolarized light image $I_T$ and the orthogonal polarized light image $I_{PV}$ that are acquired by the imaging apparatus 11. Therefore, it is possible to more accurately evaluate the skin surface condition without losing information.

2. Second Embodiment

<Block Diagram of Imaging System>

Next, an imaging system according to a second embodiment will be described.

Figure 11:
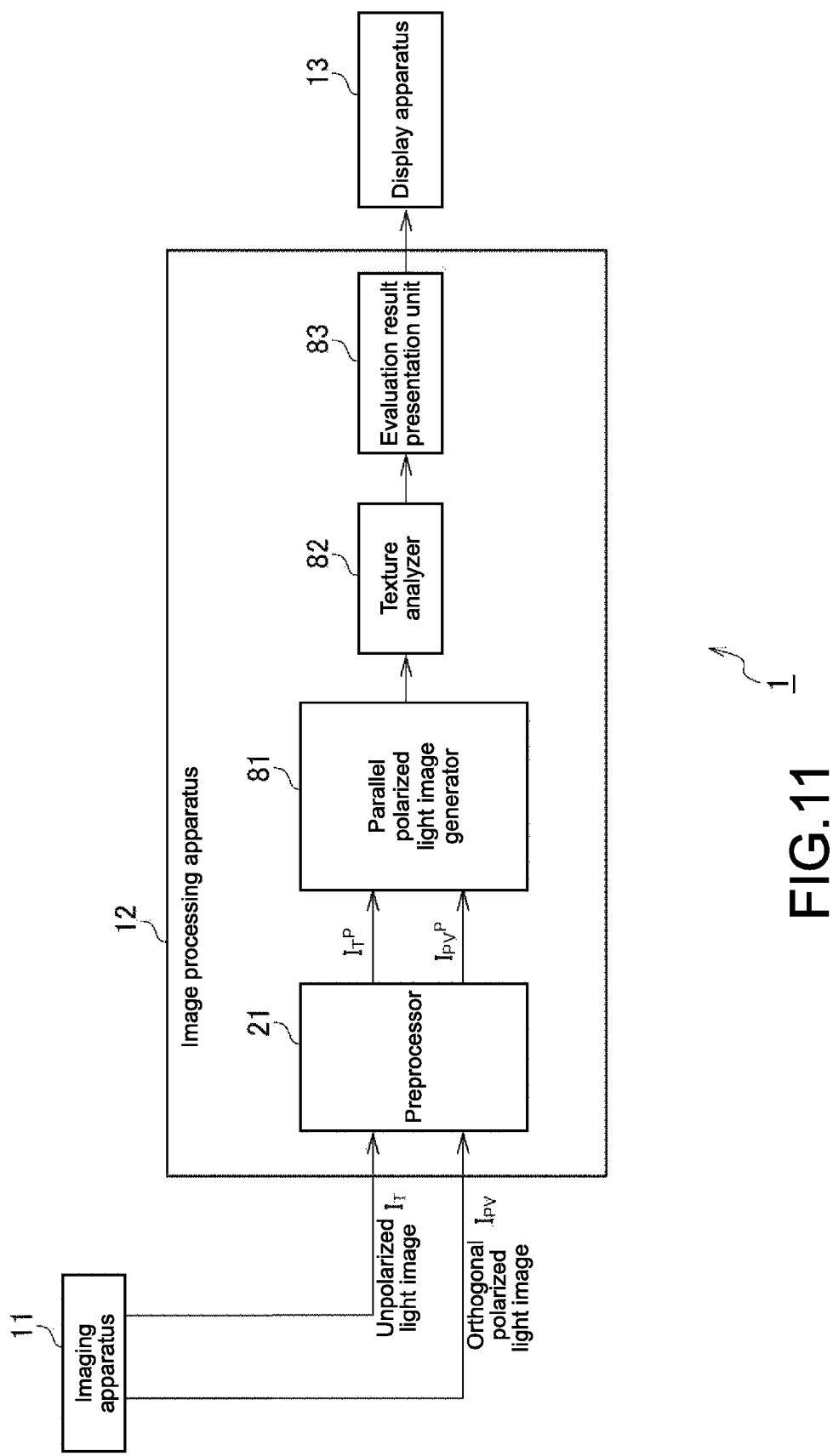
FIG. 11 is a block diagram showing an imaging system according to a second embodiment of the present disclosure.

FIG. 11 is a block diagram showing the imaging system according to the second embodiment of the present disclosure.

Note that, in FIG. 11, portions corresponding to those of the above-mentioned first embodiment will be denoted by the same reference symbols and descriptions thereof will be appropriately omitted.

As in the first embodiment, the imaging system 1 of FIG. 11 includes an imaging apparatus 11, an image processing apparatus 12, and a display apparatus 13. However, the image processing apparatus 12 has a configuration partially different from that in the first embodiment.

That is, in the second embodiment, the image processing apparatus 12 includes a preprocessor 21, a parallel polarized light image generator 81, a texture analyzer 82, and an evaluation result presentation unit 83. With this configuration, the image processing apparatus 12 evaluates a skin texture as the skin surface condition of the examinee.

Using an unpolarized light image $I_T^P$ and an orthogonal polarized light image $I_{PV}^P$ after preprocessing that are supplied from the preprocessor 21, the parallel polarized light image generator 81 generates a parallel polarized light image IPP being an image having a parallel polarized component. The parallel polarized light image generator 81 supplies the parallel polarized light image $I_{PP}$ to the texture analyzer 82.

Using the parallel polarized light image $I_{PP}$ calculated by the parallel polarized light image generator 81, the texture analyzer 82 performs texture analysis processing of analyzing the skin texture of the examinee. The texture analyzer 82 supplies the resulting analysis result to the evaluation result presentation unit 83.

Using the analysis result supplied from the texture analyzer 82, the evaluation result presentation unit 83 causes the display apparatus 13 to display information indicating the evaluation result of the skin texture condition of the examinee.

<Configuration of Parallel Polarized Light Image Generator 81>

Figure 12:
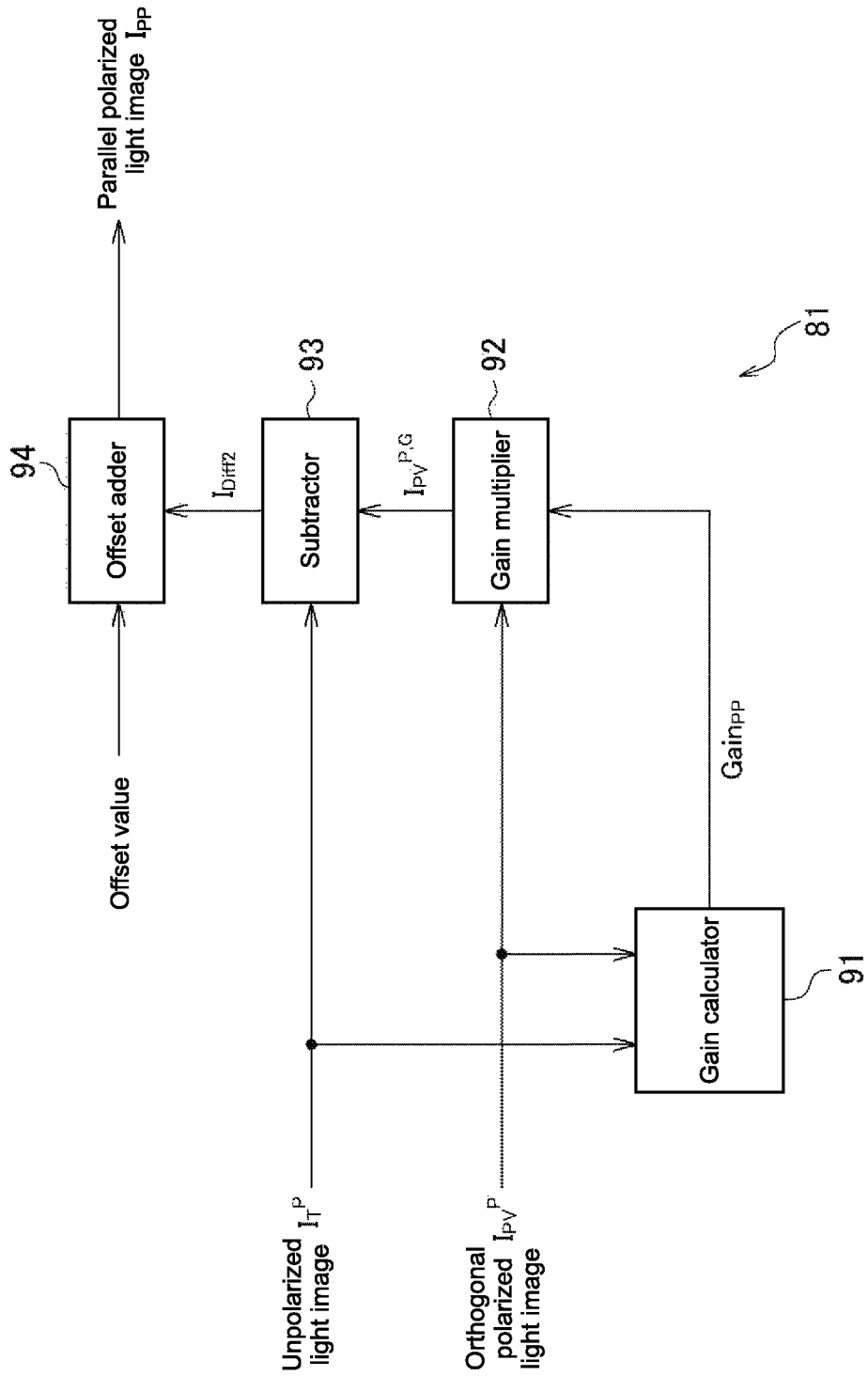
FIG. 12 is a block diagram indicating a detailed configuration example of a parallel polarized light image generator.

FIG. 12 is a block diagram showing a detailed configuration example of the parallel polarized light image generator 81.

The parallel polarized light image generator 81 includes a gain calculator 91, a gain multiplier 92, a subtractor 93, and an offset adder 94.

The unpolarized light image $I_T^P$ after preprocessing that is supplied from the preprocessor 21 is input into the gain calculator 91 and the subtractor 93 and the orthogonal polarized light image $I_{PV}^P$ after preprocessing is input into the gain calculator 91 and the gain multiplier 92.

The gain calculator 91 calculates the gain $\text{Gain}_{PP}$ to be multiplied by the gain multiplier 92 with the orthogonal polarized light image $I_{PV}^P$. The gain $\text{Gain}_{PP}$ can be calculated based on the following conception. That is, the unpolarized light image $I_T^P$ consists of a surface reflection component and an internal reflection component based on a dichromatic reflection model. The surface reflection component has a minute structure of the surface and the specular reflection component and high-frequency components are relatively dominant. In contrast, the internal reflection component indicates the color of an inside of the skin, and hence low-frequency components are dominant. Therefore, by calculating the gain $\text{Gain}_{PP}$ according to Expression (6) below, an image having the surface reflection component can be obtained.

$$\text{Gain}_{PP} = \text{argmax} \sum_{x,y} (\text{Contrast}(\Delta d(x, y))) \quad (6)$$

Argmax{ } in Expression (6) indicates a function that determines a variable that maximizes a calculated value in { }. Expression (6) shows that the gain $\text{Gain}_{PP}$ that maximizes the sum of local contrasts Contrast ($\Delta d(x, y)$) is calculated.

Here, $\Delta d(x, y)$ is an expression that is calculated according to Expression (7) below and expresses processing contents of subtraction performed by the subtractor 93 with the gain Gain being an unknown.

$$\Delta d(x,y) = I_T^P(x,y) - \text{Gain}_{PP} \cdot I_{PV}^P(x,y) \quad (7)$$

The local contrast Contrast ($\Delta d(x, y)$) is calculated according to Expression (8) by employing a method of applying a differential filter to $\Delta d(x, y)$ and obtaining a response as the local contrast.

$$\text{Contrast}(\Delta d(x, y)) = \quad (8)$$

$$\left[ \left| \begin{pmatrix} -1 & 0 & 1 \\ -1 & 0 & 1 \\ -1 & 0 & 1 \end{pmatrix} \otimes \Delta D \right| + \left| \begin{pmatrix} -1 & -1 & -1 \\ 0 & 0 & 0 \\ 1 & 1 & 1 \end{pmatrix} \otimes \Delta D \right| \right](x, y)$$

According to Expression (8), two kinds of 3*3 differential filters for the horizontal direction and the vertical direction are prepared, a convolution operation in each of the horizontal direction and the vertical direction, and values each taking an absolute value are added, to thereby determine the local contrast Contrast ($\Delta d(x, y)$). Note that, in Expression (8), $\Delta D$ indicates a universal set of $\Delta d(x, y)$ corresponding to a region of a difference image after subtraction processing performed by the subtractor 93 and the symbol of the cross (x) enclosed by the circle (○) indicates the convolution operation. Note that the local contrast Contrast ($\Delta d(x, y)$) may be calculated by a method different from Expression (8).

The calculated gain $\text{Gain}_{PP}$ is supplied from the gain calculator 91 to the gain multiplier 92.

The gain multiplier 92 multiplies, according to Expression (9) below, the gain $\text{Gain}_{PP}$ calculated by the gain calculator 91 with the orthogonal polarized light image $I_{PV}^P$ after preprocessing. The gain multiplier 92 calculates the orthogonal polarized light image $I_{PV}^{P,G}$ after the gain multiplication and supplies the orthogonal polarized light image $I_{PV}^{P,G}$ to the subtractor 93.

$$I_{PV}^{P,G}(x,y) = \text{Gain}_{PP} \cdot I_{PV}^P(x,y) \quad (9)$$

The subtractor 93 generates the difference image $I_{Diff2}$ by subtracting, according to the following Expression (10), from the unpolarized light image $I_T^P$ the orthogonal polarized light image $I_{PV}^{P,G}$ after the gain multiplication. The subtractor 93 supplies the difference image $I_{Diff2}$ to thereby generate the offset adder 94.

$$I_{Diff2}(x,y) = I_T^P(x,y) - I_{PV}^{P,G}(x,y) \quad (10)$$

The offset adder 94 calculates the parallel polarized light image $I_{PP}$ by adding an offset value std_val to a difference image $I_{Diff2}$ supplied from the subtractor 93. That is, the offset adder 94 performs a calculation according to the following Expression (11). The calculated parallel polarized light image $I_{PP}$ is supplied to the texture analyzer 82.

$$I_{PP}(x,y) = I_{Diff2}(x,y) + \text{std\_val} \quad (11)$$

<Difference Between First Embodiment and Second Embodiment>

Figure 13:
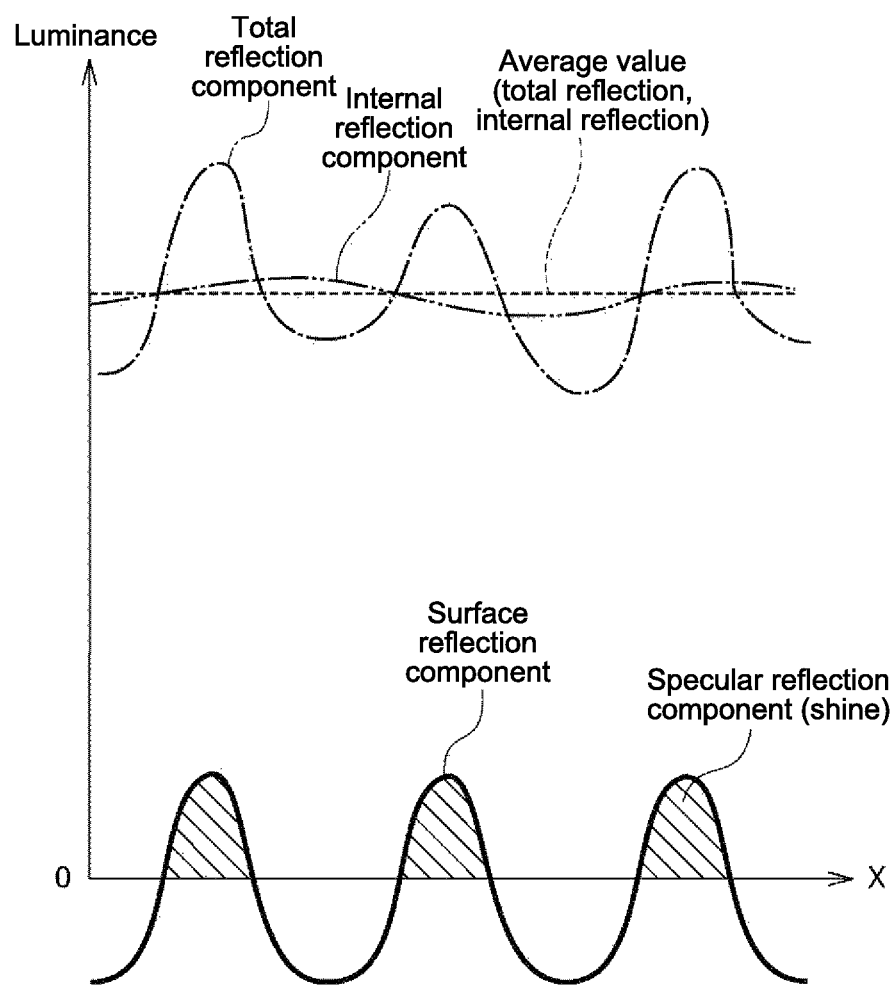
FIG. 13 is a view explaining a difference in processing between the first embodiment and the second embodiment.
Figure 14:
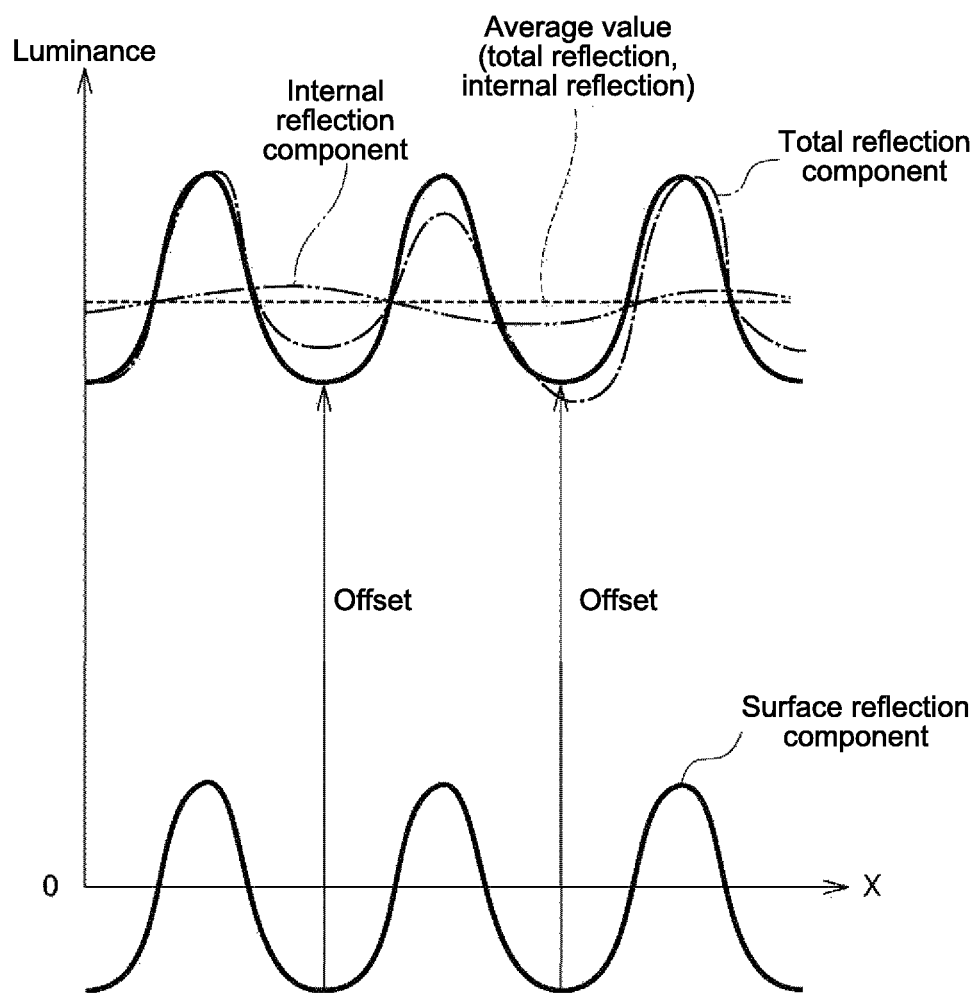
FIG. 14 is a view explaining the difference in processing between the first embodiment and the second embodiment.

Referring to FIGS. 13 and 14, a processing difference between the first embodiment and the second embodiment will be described.

FIG. 13 is a view showing a concept of a calculation of the specular reflection image $I_S$ in the above-mentioned first embodiment.

In the graph of FIG. 13, a horizontal axis indicates a pixel position x in a predetermined line of an image and a vertical axis indicates a luminance value (pixel value) in the pixel position x.

A component of light emitted to the skin of the examinee and reflected includes a surface reflection component reflected on the surface of the skin and an internal reflection component reflected after entering the skin. A total reflection component is a reflection component including both of the surface reflection component and the internal reflection component.

The total reflection component can be obtained as the unpolarized light image $I_T$ captured while causing the unpolarized light-emitting portions 42A to emit light. The internal reflection component can be obtained as the orthogonal polarized light image $I_{PV}$ captured while causing the polarized light-emitting portions 42B to emit light.

By subtracting the orthogonal polarized light image $I_{PV}$ being the internal reflection component from the unpolarized light image $I_T$ being the total reflection component, the image processing apparatus 12 according to the first embodiment calculates the specular reflection image $I_S$ being the surface reflection component shown by a solid line in FIG. 13. Positive regions of the specular reflection image $I_S$ calculated at this time, which are shown by hatching in FIG. 13, correspond to the skin shine portions.

In contrast, FIG. 14 is a view showing a concept of a calculation of the parallel polarized light image $I_{PP}$ in the second embodiment.

The parallel polarized light image generator 81 according to the second embodiment calculates the parallel polarized light image Ipp being the surface reflection component by adding the offset value std_val to the surface reflection component, which is obtained by subtracting the orthogonal polarized light image $I_{PV}$ being the internal reflection component from the unpolarized light image $I_T$ being the total reflection component, to adjust the surface reflection component to the same luminance level as that of the total reflection component or the like. Although the offset value for adjusting the surface reflection component to the same luminance level as that of the total reflection component or the like corresponds to the average value of the total reflection component (unpolarized light image $I_T$) and the internal reflection component (orthogonal polarized light image $I_{PV}$), the luminance values of the unpolarized light image $I_T$ and the orthogonal polarized light image $I_{PV}$ has been adjusted by the preprocessor 21 to the standard value std_val, and hence the standard value std_val can be used as the offset value.

<Configuration of Texture Analyzer 82>

Figure 15:
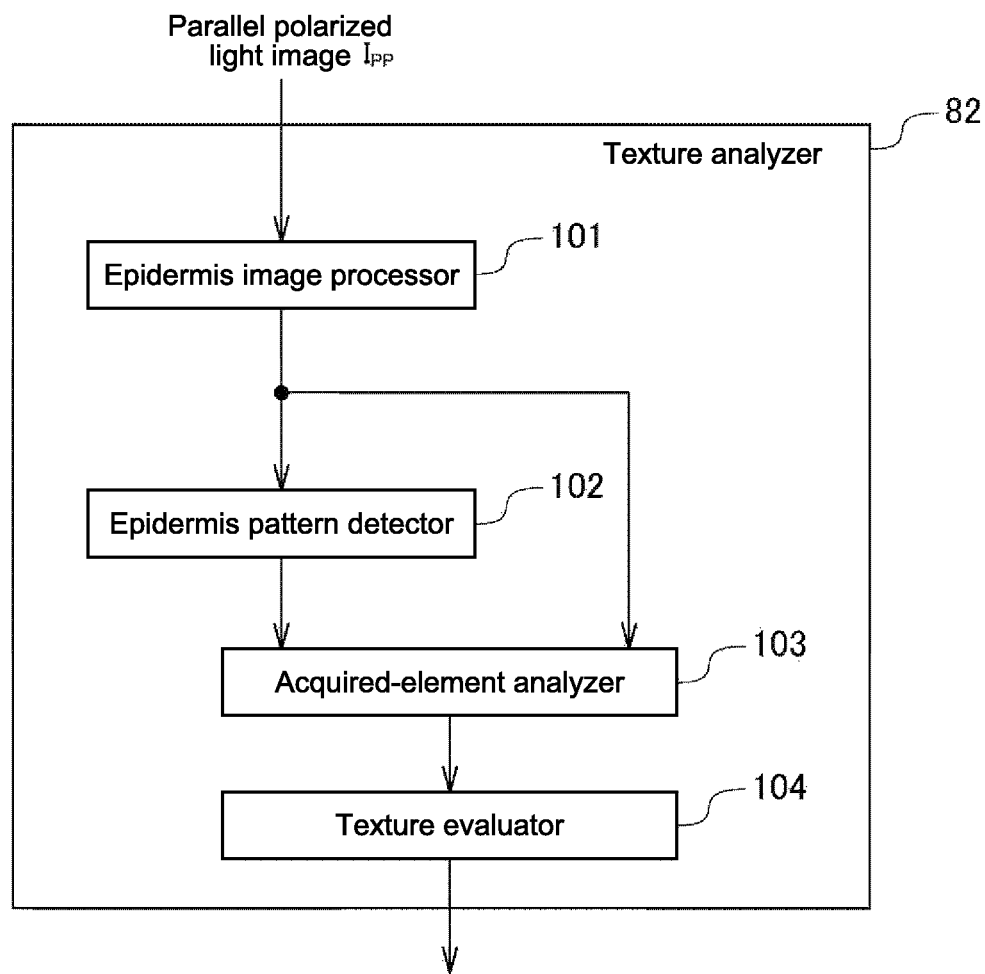
FIG. 15 is a block diagram showing a detailed configuration example of a texture analyzer.

FIG. 15 is a block diagram showing a detailed configuration example of the texture analyzer 82.

The texture analyzer 82 includes an epidermis image processor 101, an epidermis pattern detector 102, an acquired-element analyzer 103, and a texture evaluator 104.

The epidermis image processor 101 is supplied with the parallel polarized light image $I_{PP}$ calculated by the parallel polarized light image generator 81. Note that the parallel polarized light image $I_{PP}$ will be also referred to as an epidermis image in the following description.

The epidermis image processor 101 subjects the epidermis image to predetermined image processing such as correction and noise removal. The epidermis image processor 101 supplies the epidermis image after image processing to the epidermis pattern detector 102 and the acquired-element analyzer 103.

The epidermis pattern detector 102 detects a pattern of an epidermis (hereinafter, referred to as epidermis pattern) in the epidermis image, which is formed of furrows (sulcus cutises) and ridges (crista cutises) on an epidermis. The epidermis pattern detector 102 detects a detection result (hereinafter, referred to as epidermis pattern detection result) to the acquired-element analyzer 103.

The acquired-element analyzer 103 analyzes, based on the epidermis image after image processing and the epidermis pattern detection result, acquired elements out of elements indicating the skin texture condition. The acquired-element analyzer 103 supplies an analysis result to the texture evaluator 104.

The texture evaluator 104 evaluates the skin texture condition of the examinee based on the analysis result by the acquired-element analyzer 103. The texture evaluator 104 supplies an evaluation result to the evaluation result presentation unit 83 (FIG. 11).

<Configurations of Epidermis Image Processor 101 and Epidermis Pattern Detector 102>

Figure 16:
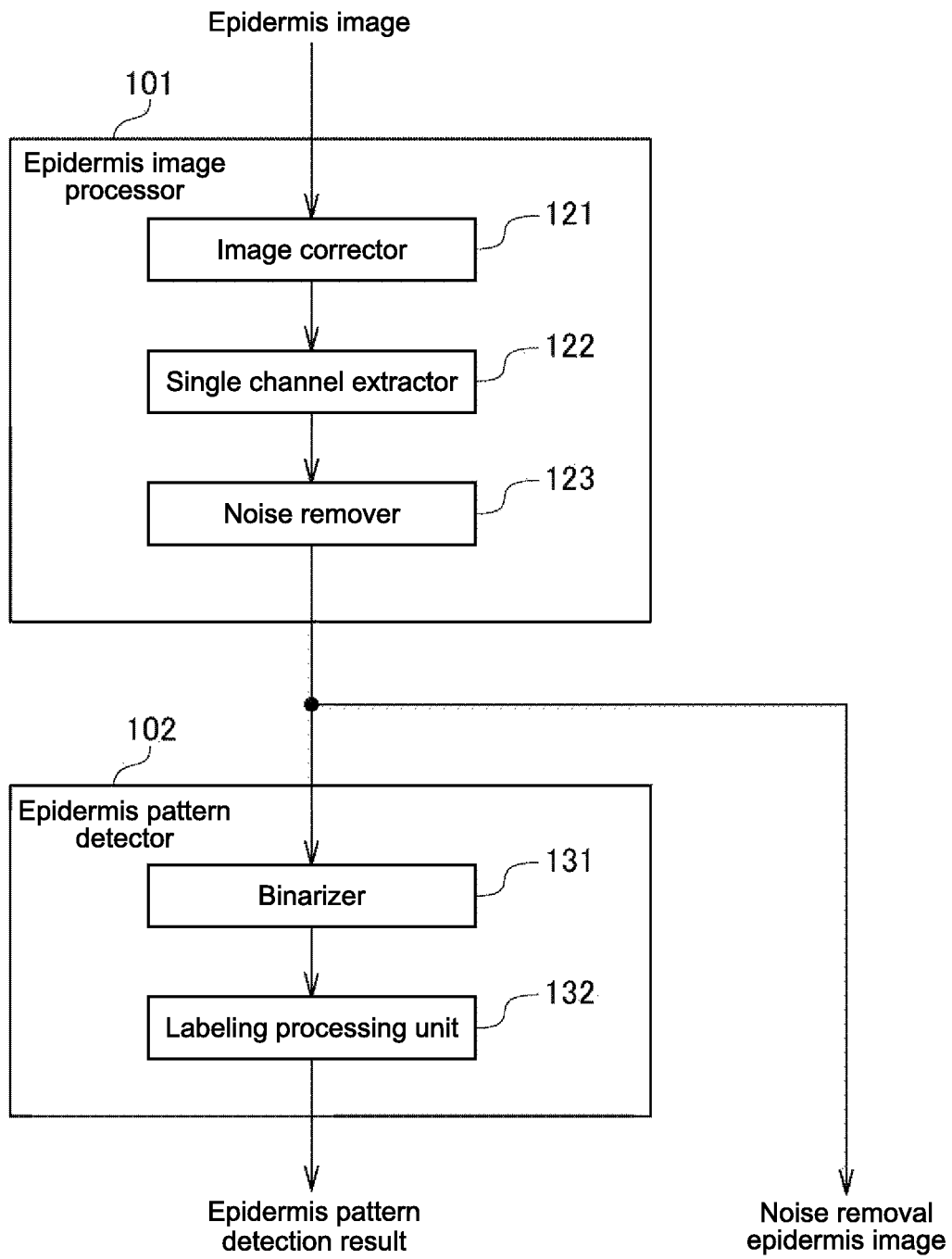
FIG. 16 is a block diagram showing functional configuration examples of an epidermis image processor and an epidermis pattern detector.

FIG. 16 is a block diagram showing a function configuration example of the epidermis image processor 101 and the epidermis pattern detector 102.

The epidermis image processor 101 includes an image corrector 121, a single channel extractor 122, and a noise remover 123. In addition, the epidermis pattern detector 102 includes a binarizer 131 and a labeling processing unit 132.

The image corrector 121 performs predetermined image correction such as distortion correction and reduction of the epidermis image. The image corrector 121 supplies the epidermis image after the correction to the single channel extractor 122.

The single channel extractor 122 extracts a signal component of a predetermined channel from the corrected epidermis image. The single channel extractor 122 supplies an epidermis image of the extracted signal component (hereinafter, referred to as single-channel epidermis image) to the noise remover 123.

The noise remover 123 removes noise from the single-channel epidermis image. The noise remover 123 supplies the single-channel epidermis image after the noise removal (hereinafter, referred to as noise-removed epidermis image) to the binarizer 131 of the epidermis pattern detector 102 and the acquired-element analyzer 103.

The binarizer 131 performs binarization processing on the noise-removed epidermis image. The binarizer 131 supplies the resulting binarized image (hereinafter, referred to as binarized epidermis image) to the labeling processing unit 132.

The labeling processing unit 132 detects the epidermis pattern by performing labeling processing on the binarized epidermis image. More specifically, the labeling processing unit 132 detects regions of ridges (hereinafter, referred to as ridge regions) in the epidermis image as the epidermis pattern. Further, the labeling processing unit 132 counts the number of ridge regions in the epidermis image. Further, the labeling processing unit 132 supplies the acquired-element analyzer 103 with an epidermis pattern detection result indicating a detection result of the ridge regions and the number of ridges.

<Configuration Example of Acquired-Element Analyzer 103>

Figure 17:
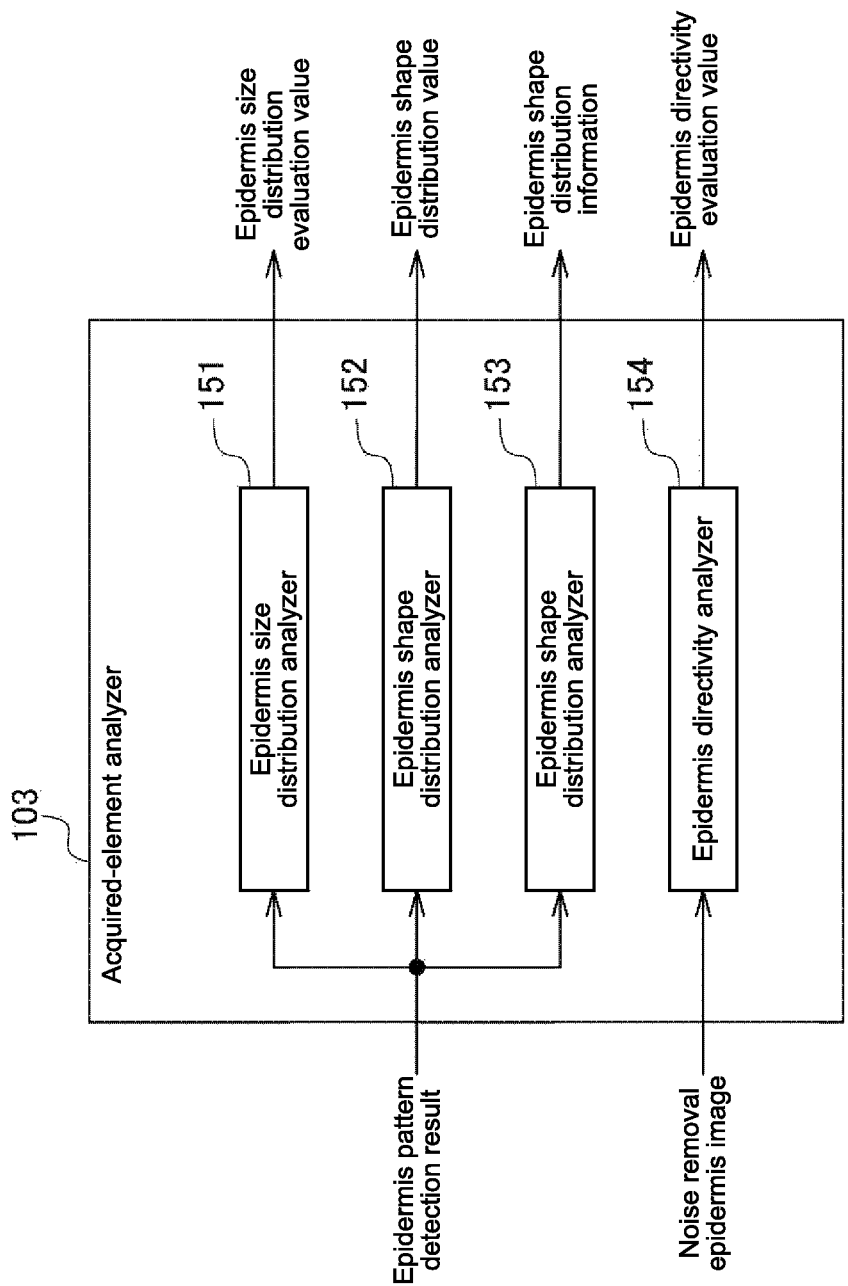
FIG. 17 is a block diagram showing a functional configuration example of an acquired-element analyzer.

FIG. 17 is a block diagram showing a function configuration example of the acquired-element analyzer 103.

The acquired-element analyzer 103 includes an epidermis size distribution analyzer 151, an epidermis shape distribution analyzer 152, an epidermis shape distribution analyzer 153, and an epidermis directivity analyzer 154.

The epidermis size distribution analyzer 151 analyzes a distribution of sizes of the epidermis pattern. More specifically, the epidermis size distribution analyzer 151 analyzes a distribution of sizes of the ridge regions and calculates an epidermis size distribution evaluation value indicating uniformity of the sizes of the ridge regions. The epidermis size distribution analyzer 151 supplies the calculated epidermis size distribution evaluation value to the texture evaluator 104.

The epidermis shape distribution analyzer 152 analyzes a distribution of shapes of the epidermis pattern. More specifically, the epidermis shape distribution analyzer 152 analyzes a distribution of shapes of the ridge regions and calculates an epidermis shape distribution evaluation value indicating uniformity of the shapes of the ridge regions. The epidermis shape distribution analyzer 152 supplies the calculated epidermis shape distribution evaluation value to the texture evaluator 104.

The epidermis shape distribution analyzer 153 analyzes a distribution of shapes of the epidermis pattern from a perspective different from that of the epidermis shape distribution analyzer 152. More specifically, the epidermis shape distribution analyzer 153 compares each ridge region with a predetermined reference shape and determines epidermis shape distribution information indicating a ratio at which the ridge regions have shapes similar to the reference shape. The epidermis shape distribution analyzer 153 supplies the determined epidermis shape distribution information to the texture evaluator 104.

The epidermis directivity analyzer 154 analyzes directivity of the epidermis pattern. More specifically, the epidermis directivity analyzer 154 analyzes a distribution of edge directions of the ridge regions by applying edge filters of four directions of, for example, 0 degrees, 45 degrees, 90 degrees, and 135 degrees to the noise-removed epidermis image, and calculates an epidermis directivity evaluation value indicating uniformity of the distribution of the edge directions of the ridge regions. The epidermis directivity analyzer 154 supplies the calculated epidermis directivity evaluation value to the texture evaluator 104.

Note that the sizes, shapes, edge directions of the ridges change in an acquired manner due to aging, health condition, skin care, and the like. Therefore, the epidermis size distribution evaluation value, the epidermis shape distribution evaluation value, the epidermis shape distribution information, and the epidermis directivity evaluation value are indexes for evaluating acquired characteristics of the skin texture condition.

<Skin Texture Evaluation Processing>

Next, referring to a flowchart in FIG. 18, skin texture evaluation processing in the imaging system according to the second embodiment will be described.

First, in Step S21, the imaging apparatus 11 captures a skin image. Specifically, the imaging apparatus 11 generates two kinds of (two) images of the unpolarized light image $I_T$ and the orthogonal polarized light image $I_{PV}$ by imaging the skin of the examinee while causing the unpolarized light-emitting portions 42A and the polarized light-emitting portions 42B to emit light in a time division manner. The imaging apparatus 11 supplies the resulting captured images to the image processing apparatus 12.

In Step S22, the preprocessor 21 performs preprocessing for making it easy to perform processing at the subsequent stages on the unpolarized light image $I_T$ and the orthogonal polarized light image $I_{PV}$ supplied from the imaging apparatus 11. Specifically, the preprocessor 21 adjusts luminance values according to Expressions (1) and (2) such that the images take an optimal average luminance value. The unpolarized light image $I_T^P$ and the orthogonal polarized light image $I_{PV}^P$ after preprocessing are supplied to the parallel polarized light image generator 81.

In Step S23, the gain calculator 91 of the parallel polarized light image generator 81 calculates the gain Gainpp to be multiplied by the gain multiplier 92 with the orthogonal polarized light image $I_{PV}^P$.

In Step S24, the gain multiplier 92 multiplies the gain Gainpp calculated by the gain calculator 91 with the orthogonal polarized light image $I_{PV}^P$ after preprocessing, and supplies the orthogonal polarized light image $I_{PV}^{P, G}$ after the gain multiplication to the subtractor 93. Specifically, the gain multiplier 92 performs the calculation according to Expression (9) above.

In Step S25, the subtractor 93 generates the difference image $I_{Diff2}$ by subtracting from the unpolarized light image $I_T^P$ the orthogonal polarized light image $I_{PV}^{P, G}$ after the gain multiplication and supplies the difference image $I_{Diff2}$ to the offset adder 94. That is, the subtractor 93 performs the calculation according to Expression (10) above with each pixel of the unpolarized light image $I_T^P$.

In Step S26, the offset adder 94 generates the parallel polarized light image $I_{PP}$ by adding the offset value std_val to the difference image $I_{Diff2}$ according to Expression (11). Then, the offset adder 94 supplies the generated parallel polarized light image $I_{PP}$ to the texture analyzer 82.

In Step S27, the texture analyzer 82 executes texture analysis processing of analyzing the skin texture of the examinee using the parallel polarized light image $I_{PP}$ (epidermis image) generated in Step S26 and supplies the resulting analysis result to the evaluation result presentation unit 83. Details of texture analysis processing in Step S27 will be described later with reference to FIG. 19 and the like.

In Step S28, the evaluation result presentation unit 83 causes the display apparatus 13 to display information indicating the evaluation result of the skin texture condition of the examinee using the analysis result supplied from the texture analyzer 82 and terminates processing.

<Texture Analysis Processing>

Figure 18:
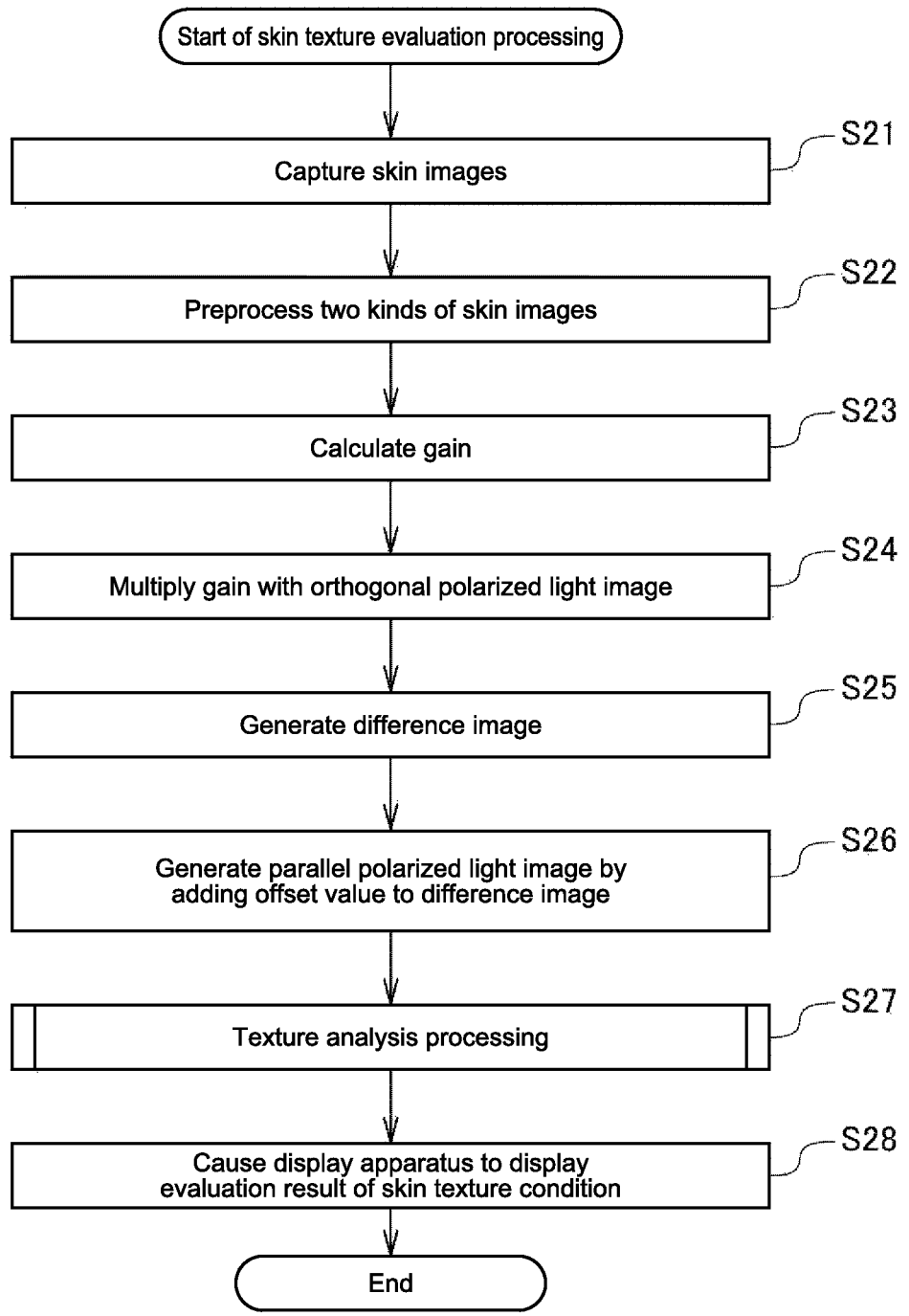
FIG. 18 is a flowchart explaining skin texture evaluation processing in the imaging system according to the second embodiment.
Figure 19:
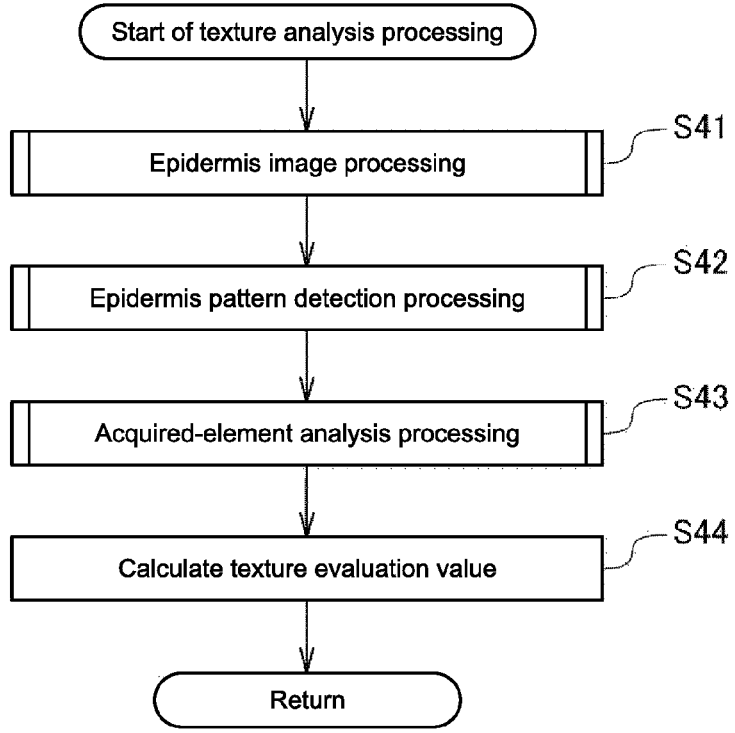
FIG. 19 is a flowchart explaining details of texture analysis processing.

FIG. 19 shows a detailed flowchart of texture analysis processing in Step S27 of FIG. 18.

In processing, first, in Step S41, the epidermis image processor 101 performs epidermis image processing of subjecting the parallel polarized light image $I_{PP}$ as the epidermis image to predetermined image processing such as correction and noise removal. Details of epidermis image processing will be described with reference to FIG. 20.

In Step S42, the epidermis pattern detector 102 detects an epidermis pattern in the epidermis image, which is formed of ridges or furrows on an epidermis, and performs epidermis pattern detection processing of outputting the epidermis pattern detection result being the detection result. Details of epidermis pattern detection processing will be described later with reference to FIG. 21.

In Step S43, the acquired-element analyzer 103 performs, based on the epidermis image after image processing and the epidermis pattern detection result, acquired-element analysis processing of analyzing acquired elements out of elements indicating the skin texture condition. Details of acquired-element analysis processing will be described later with reference to FIG. 22.

In Step S44, the texture evaluator 104 evaluates, based on the analysis result by the acquired-element analyzer 103, the skin texture condition of the examinee and calculates a texture evaluation value as the evaluation result. The calculated texture evaluation value is supplied to the evaluation result presentation unit 83. Texture analysis processing is terminated. Processing proceeds to Step S28, referring back to FIG. 18.

In this manner, the skin texture condition can be evaluated based on the uniformity of the texture and the shapes of the ridges being the acquired elements indicating the skin texture condition. As a result, it is possible to more accurately evaluate the skin texture condition.

<Epidermis Image Processing>

Figure 20:
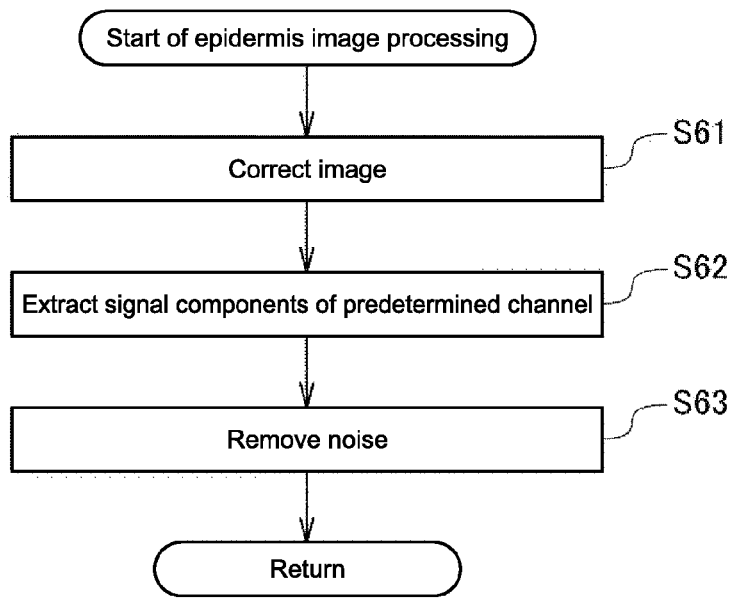
FIG. 20 is a flowchart explaining details of epidermis image processing.

Next, referring to the flowchart of FIG. 20, epidermis image processing in Step S41 of FIG. 19 will be described in detail.

In Step S61, the image corrector 121 corrects an image. For example, it is assumed that shading distortion, lens distortion, and the like are generated at a periphery of the epidermis image. Therefore, the image corrector 121 performs, for example, shading correction and lens distortion correction on the epidermis image or cuts out a center region of the epidermis image.

For example, in order to reduce the processing costs, the image corrector 121 reduces the image after the correction.

Hereinafter, it is assumed that the epidermis image after the correction has a size of vertical 160 pixels horizontal 120 pixels unless otherwise specifically noted.

The image corrector 121 supplies the epidermis image after the correction to the single channel extractor 122.

In Step S62, the single channel extractor 122 extracts signal components of a predetermined channel from the corrected epidermis image. For example, the single channel extractor 122 extracts signal components of a B (blue) channel from the corrected epidermis image. Then, the single channel extractor 122 supplies the noise remover 123 with the single-channel epidermis image composed of the extracted signal components.

In Step S63, the noise remover 123 removes noise from the single-channel epidermis image. For example, the noise remover 123 applies a smoothing filter to the single-channel epidermis image.

More specifically, in order to remove random noise and texture components on the ridges or the furrows, for example, the noise remover 123 applies an edge-preserving smoothing filter to the single-channel epidermis image. As this edge-preserving smoothing filter, a bilateral filter having a kernel size of 3*3 pixels and $\sigma_{space}$=15 and $\sigma_{color}$=15 is used, for example.

Next, for example, in order to remove the high luminance region and the specular reflection component due to influences of sweat glands and the like, the noise remover 123 applies an isolated point removal filter to the single-channel epidermis image. As this isolated point removal filter, a median filter having 3*3 pixels is used, for example.

Note that such noise removal processing largely depends on the imaging environment and the performance of the imaging apparatus 11, and hence it is desirable to appropriately change an applied filter, parameters, and the like depending on the imaging environment and the performance of the imaging apparatus 11.

Thus, the noise remover 123 supplies the noise-removed epidermis image being the single-channel epidermis image after the noise removal to the binarizer 131 of the epidermis pattern detector 102 and the epidermis directivity analyzer 154 of the acquired-element analyzer 103.

Then, epidermis image processing is terminated and processing returns to texture analysis processing in FIG. 19.

<Epidermis Pattern Detection Processing>

Figure 21:
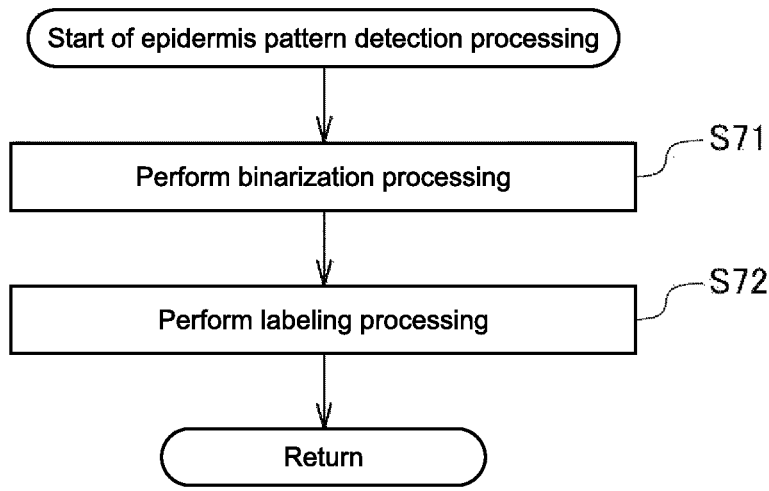
FIG. 21 is a flowchart explaining details of epidermis pattern detection processing.

Next, referring to the flowchart of FIG. 21, epidermis pattern detection processing in Step S42 of FIG. 19 will be described in detail.

In Step S71, the binarizer 131 performs binarization processing. Specifically, assuming that a bright region of the epidermis image is a ridge on a front side and a dark region of the epidermis image is a furrow on a deep side under a uniform light source, the binarizer 131 binarizes the noise-removed epidermis image in order to perform segmentation of the ridges and the furrows. Then, the binarizer 131 supplies the binarized epidermis image obtained by binarizing the noise-removed epidermis image to the labeling processing unit 132.

In Step S72, the labeling processing unit 132 performs 4 or 8-coupled labeling processing on the binarized epidermis image from the outside. At this time, the labeling processing unit 132 detects a region surrounded by an outermost white outline as one region and ignores a black region or a region surrounded by another while outline within this region even if it is present. With this, for example, a region that is dark due to the presence of a recess within the ridge and the like is ignored, and hence it is possible to accurately detect the ridge regions.

Note that, hereinafter, regions labeled in labeling processing will be referred to as labelling regions.

Further, an interval between furrows of an average human skin is 0.25 to 0.5 mm. Considering the fact that most of the ridges have triangle or square shapes, it is assumed that a ridge has an area of from approximately 0.031 to 0.25 mm².

Therefore, the labeling processing unit 132 calculates an appropriate range of a size of a ridge in an epidermis image based on the size or the like of the image sensor 43 of the imaging apparatus 11. Then, the labeling processing unit 132 detects, from the detected labelling regions, regions each having a size within the calculated appropriate range as the ridge regions.

Further, the labeling processing unit 132 counts the number of detected ridge regions as the number of ridges $N_{ridge}$.

Then, the labeling processing unit 132 supplies an epidermis pattern detection result indicating the detection result of the ridge regions and the number of ridges $N_{ridge}$ to the epidermis size distribution analyzer 151, the epidermis shape distribution analyzer 152, and the epidermis shape distribution analyzer 153 of the acquired-element analyzer 103.

Then, epidermis pattern detection processing is terminated. Texture analysis processing in FIG. 19 will be returned.

<Acquired-Element Analysis Processing>

Figure 22:
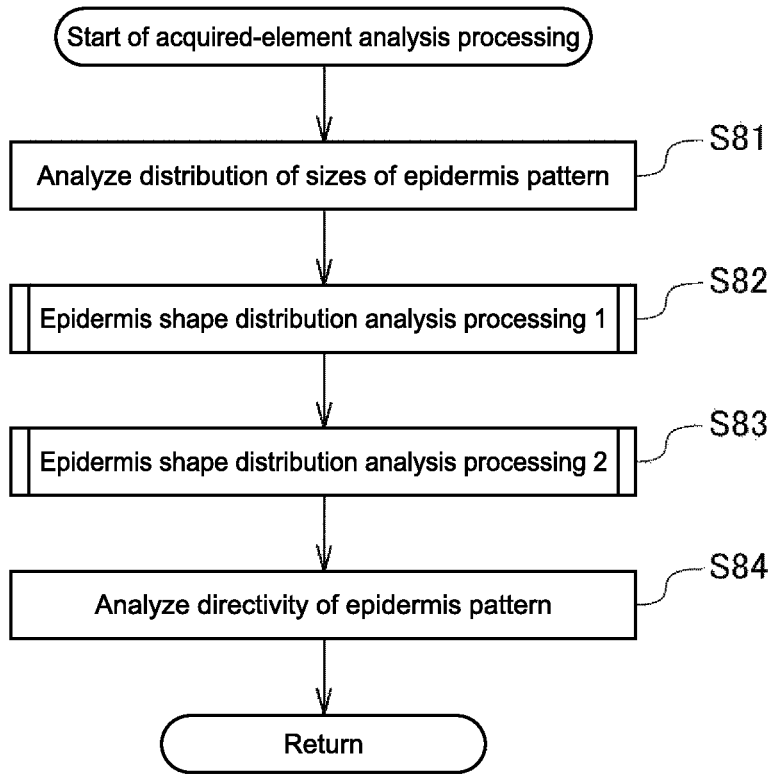
FIG. 22 is a flowchart explaining details of acquired-element analysis processing.

Next, referring to the flowchart of FIG. 22, acquired-element analysis processing in Step S43 of FIG. 19 will be described in detail.

In Step S81, the epidermis size distribution analyzer 151 analyzes a distribution of sizes of the epidermis pattern.

Figure 23:
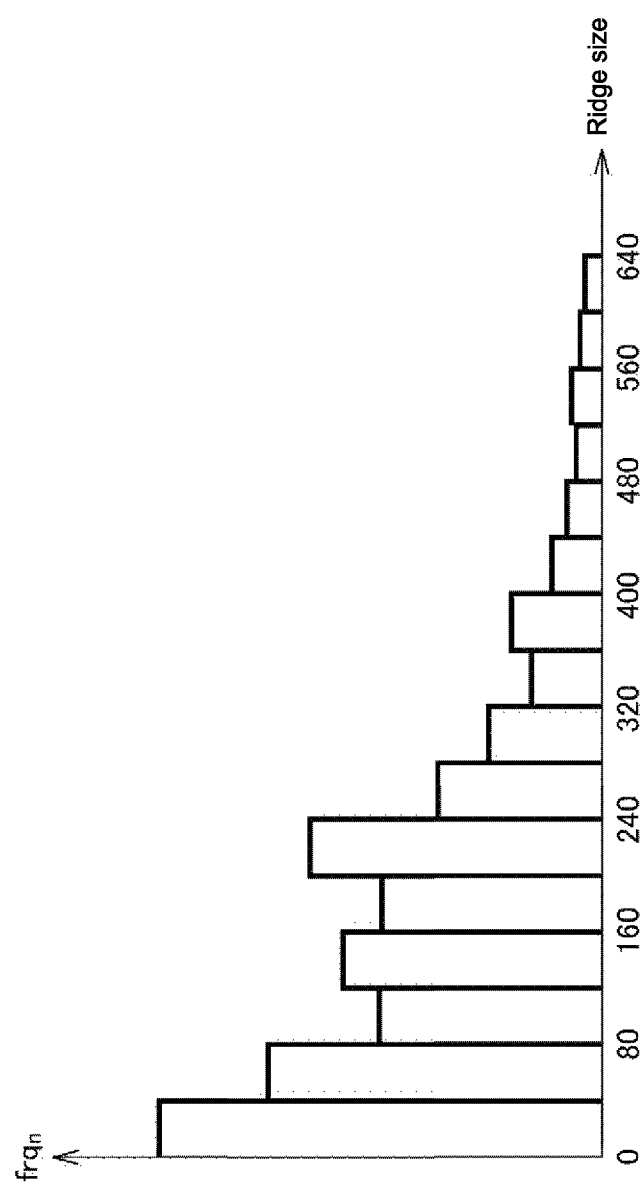
FIG. 23 is a view showing an example of a histogram of a size of a ridge region.

Specifically, first, the epidermis size distribution analyzer 151 creates a histogram of the size of the ridge region. FIG. 23 shows an example of the histogram of the size (area) of the ridge region. In the figure, a horizontal axis indicates a size of the ridge region and a vertical axis indicates a frequency $frq_n$ of each bin of a histogram.

Next, the epidermis size distribution analyzer 151 calculates an average value $H_{avg}$ of sizes of the ridge regions according to the following Expression (12).

$$H_{avg} = \frac{\sum_{n}(n \cdot frq_n)}{\sum_{n}(frq_n)} \tag{12}$$

Note that n indicates a median of each bin.

Further, the epidermis size distribution analyzer 151 calculates a variance $H_{var}$ of the sizes of the ridge regions according to the following Expression (13).

$$H_{var} = \frac{\sum_{n}((n - H_{avg})^2 \cdot frq_n)}{\sum_{n}(frq_n)} \tag{13}$$

Figure 24:
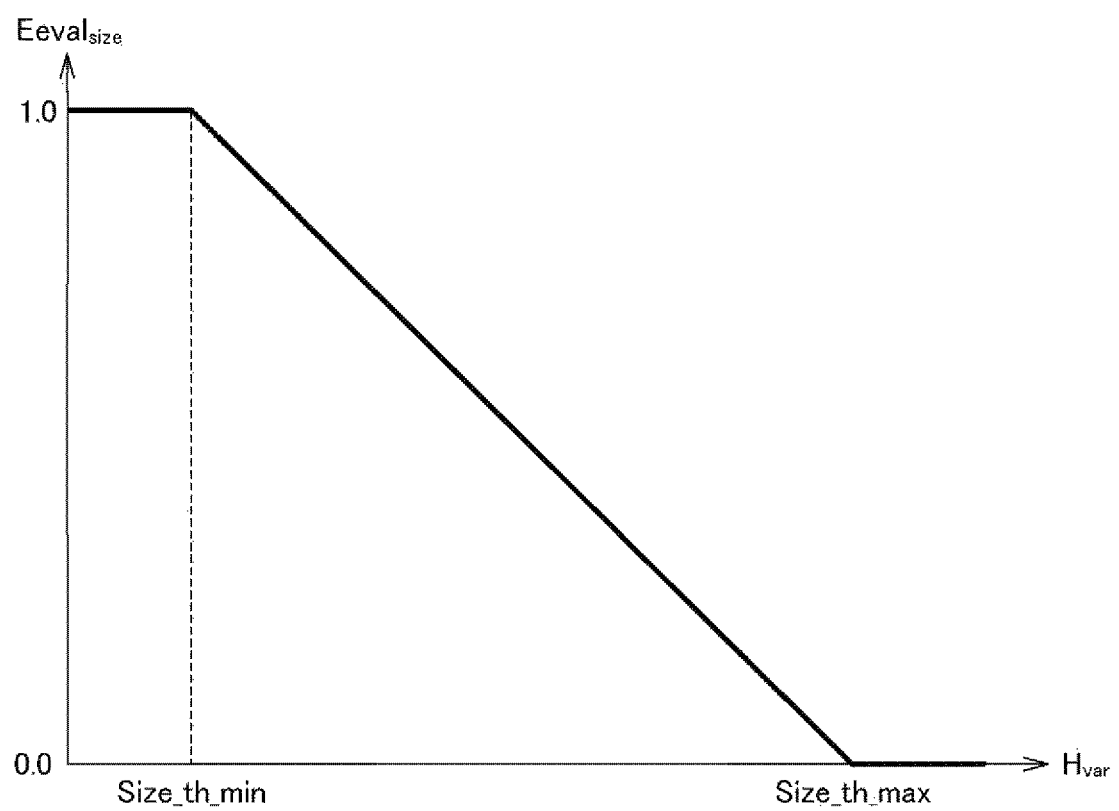
FIG. 24 is a view showing an example of a normalization curve of an epidermis size distribution analyzer.

In addition, the epidermis size distribution analyzer 151 calculates, based on a normalization curve shown in FIG. 24, an epidermis size distribution evaluation value $Eeval_{size}$ where the variance $H_{var}$ is normalized to a range of from 0 to 1. In the figure, Size_th_min and Size_th_max are threshold values each of which determines the normalization curve.

The epidermis size distribution evaluation value $Eeval_{size}$ increases as the variance $H_{var}$ of the sizes of the ridge regions decreases. In other words, the epidermis size distribution evaluation value $Eeval_{size}$ increases as a variation of the sizes of the ridge regions decreases. Thus, the epidermis size distribution evaluation value $Eeval_{size}$ is an index indicating the uniformity of the sizes of the ridge regions.

The epidermis size distribution analyzer 151 supplies the epidermis size distribution evaluation value $Eeval_{size}$ to the texture evaluator 104.

In Step S82, the epidermis shape distribution analyzer 152 performs epidermis shape distribution analysis processing 1.

<Epidermis Shape Distribution Analysis Processing 1>

Figure 25:
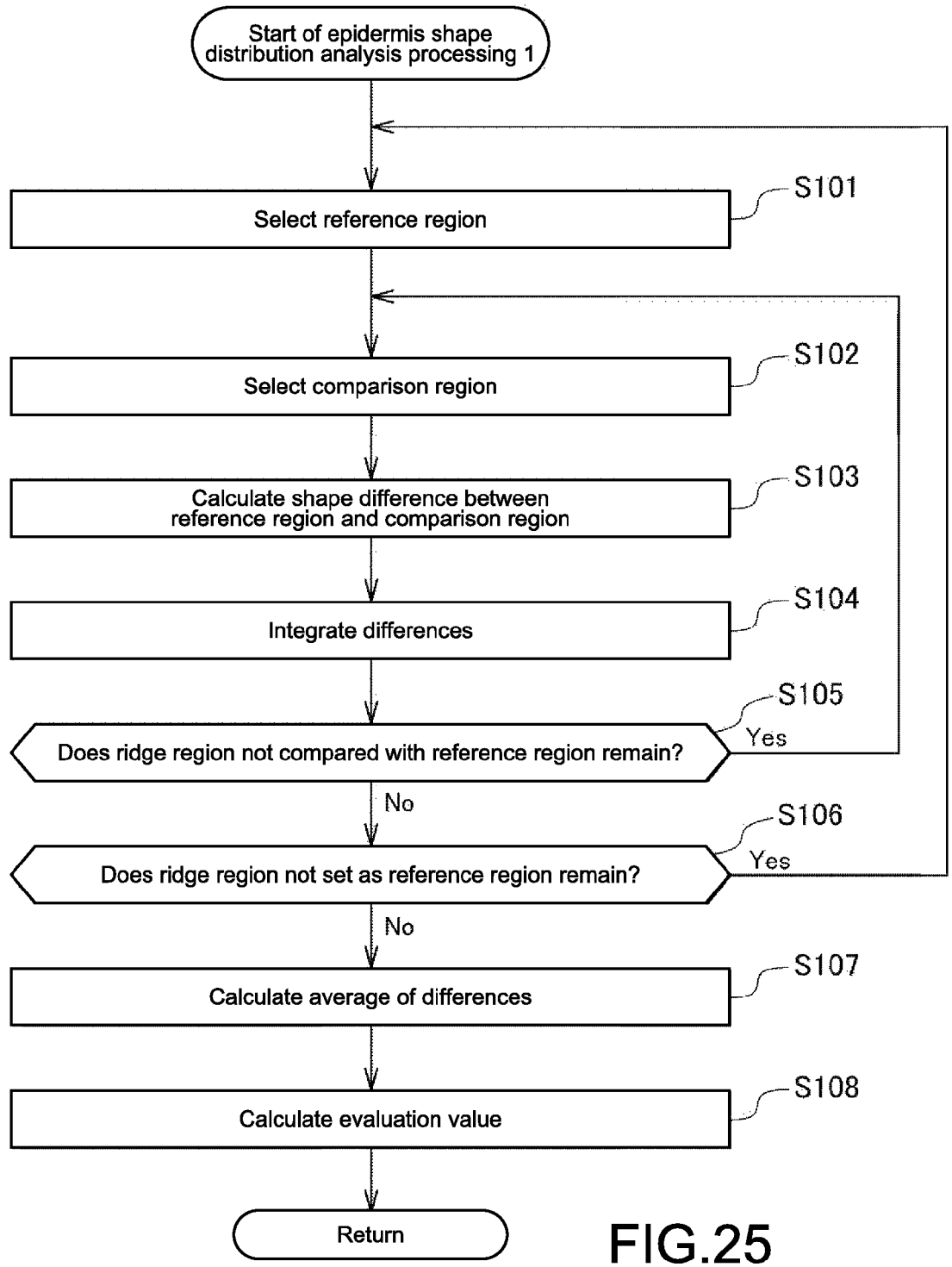
FIG. 25 is a flowchart explaining details of epidermis shape distribution analysis processing 1.

Now, referring to the flowchart of FIG. 25, epidermis shape distribution analysis processing 1 in Step S82 will be described in detail.

In Step S101, the epidermis shape distribution analyzer 152 selects a reference region. Specifically, the epidermis shape distribution analyzer 152 selects one ridge region which has not been yet set as the reference region and set the ridge region as the reference region.

In Step S102, the epidermis shape distribution analyzer 152 selects a comparison region. Specifically, the epidermis shape distribution analyzer 152 selects one ridge region the shape of which has not been yet compared with that of the reference region and sets the ridge region as the comparison region.

In Step S103, the epidermis shape distribution analyzer 152 calculates a shape difference between the reference region and the comparison region.

For example, the epidermis shape distribution analyzer 152 digitalizes shapes of the reference region and the comparison region using Hu invariant moments and calculates a shape difference between the reference region and the comparison region based on the digitalized values. Although the method of calculating the difference is not particularly limited, the difference decreases as the shape of the reference region and the shape of the comparison region becomes more similar to each other.

Note that details of the Hu invariant moments are described in, for example, "Visual Pattern Recognition by Moment Invariants," by M-K. Hu. IRE Trans. action on Information Theory, February 1962, Volume 8, pp. 179-187.

In Step S104, the epidermis shape distribution analyzer 152 integrates differences. Specifically, the epidermis shape distribution analyzer 152 adds a newly calculated difference to the already calculated integrated value of the differences of the ridge regions.

In Step S105, the epidermis shape distribution analyzer 152 determines whether or not a ridge region not compared with the reference region remains. If it is determined that the ridge region not compared with the reference region remains, processing returns to Step S102.

After that, in Step S105, until it is determined that the ridge region not compared with the reference region does not remain, processing of from Steps S102 to S105 is repeatedly performed.

If it is determined in Step S105 that the ridge region not compared with the reference region does not remain, processing proceeds to Step S106.

In Step S106, the epidermis shape distribution analyzer 152 determines whether or not a ridge region not set as the reference region remains. If it is determined that the ridge region not set as the reference region remains, processing returns to Step S101.

After that, until it is determined in Step S106 that the ridge region not set as the reference region does not remain, processing of from Steps S101 to S106 is repeatedly performed. As a result, differences are calculated with respect to all combinations of the ridge regions and a cumulative addition value of the differences is further calculated.

If it is determined in Step S106 that the ridge region not set as the reference region does not remain, processing proceeds to Step S107.

In Step S107, the epidermis shape distribution analyzer 152 calculates a difference average $Diff_{avg}$ according to the following Expression (14).

$$Diff_{avg} = \frac{\sum_{i=0}^{N_{ridge}-1} \sum_{j=i+1}^{N_{ridge}-1} D(R_i, R_j)}{N_{comp}} \tag{14}$$

Note that $R_i$ and $R_j$ indicate ridge regions of a label i and a label j, respectively. Thus, a denominator on the right side of Expression (14) becomes the cumulative addition value of the shape differences of all the combinations of the ridge regions. Further, $N_{comp}$ is calculated according to the following Expression (15) and indicates the number of comparisons of the shapes of the ridge regions.

$$N_{comp} = \frac{N_{ridge}(N_{ridge} - 1)}{2} \tag{15}$$

Figure 26:
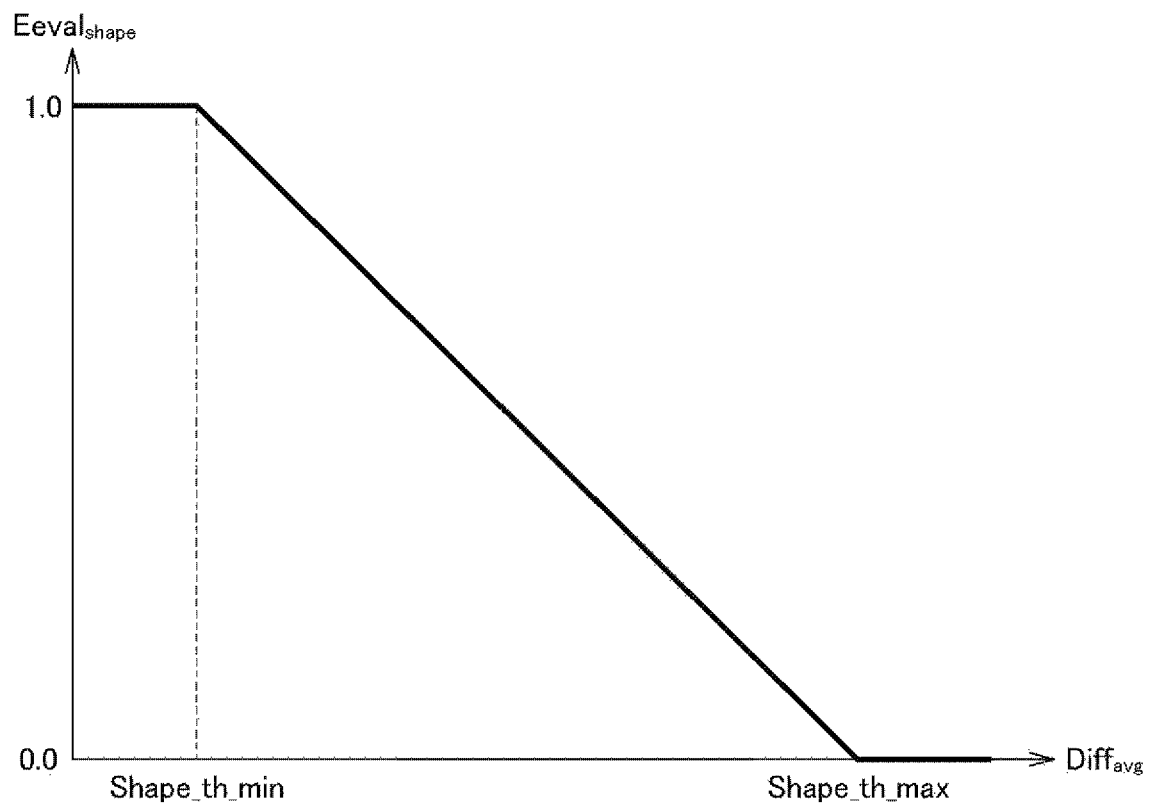
FIG. 26 is a view showing an example of a normalization curve of an epidermis shape distribution analyzer.

In Step S108, the epidermis shape distribution analyzer 152 calculates an evaluation value. Specifically, the epidermis shape distribution analyzer 152 calculates, based on a normalization curve shown in FIG. 26, an epidermis shape distribution evaluation value $Eeval_{shape}$ where the difference average $Diff_{avg}$ is normalized to a range of from 0 to 1. In the figure, Shape_th_min and Shape_th_max are threshold values each of which determines the normalization curve.

The epidermis shape distribution evaluation value $Eeval_{shape}$ increases as the difference average $Diff_{avg}$ of the shapes of the ridge regions decreases. In other words, the epidermis shape distribution evaluation value $Eeval_{shape}$ increases as a variation in the shapes of the ridge regions decreases. Thus, the epidermis shape distribution evaluation value $Eeval_{shape}$ is an index indicating uniformity of the shapes of the ridge regions.

The epidermis shape distribution analyzer 152 supplies the epidermis shape distribution evaluation value $Eeval_{shape}$ to the texture evaluator 104.

After that, epidermis shape distribution analysis processing 1 is terminated.

Referring back to FIG. 22, in Step S83, the epidermis shape distribution analyzer 153 performs epidermis shape distribution analysis processing 2.

<Epidermis Shape Distribution Analysis Processing 2>

Figure 27:
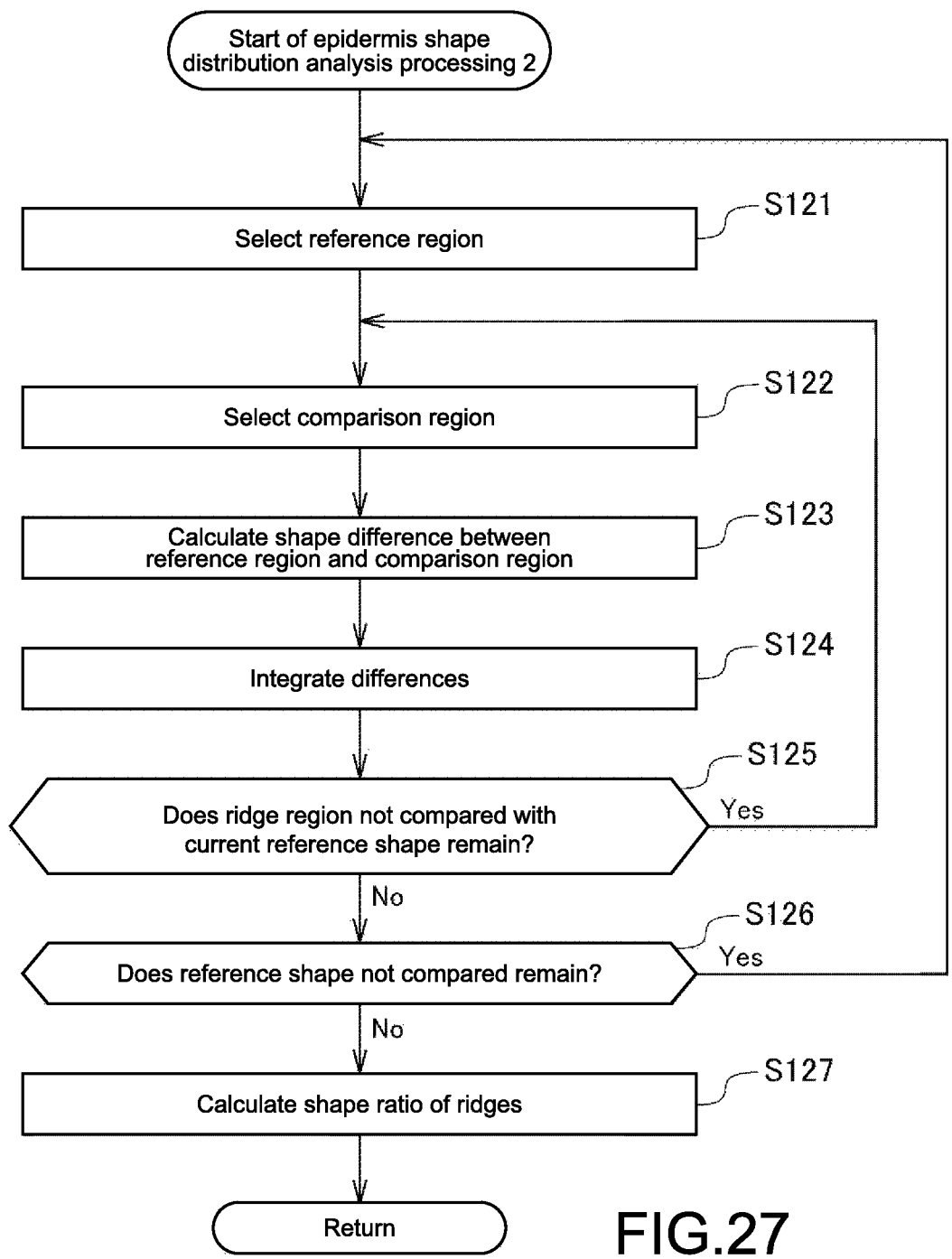
FIG. 27 is a flowchart explaining details of epidermis shape distribution analysis processing 2.

Now, referring to the flowchart of FIG. 27, epidermis shape distribution analysis processing 2 in Step S83 will be described in detail.

In Step S121, the epidermis shape distribution analyzer 153 selects a reference shape.

In general, it is ideal that the ridges have triangle or diamond shapes. In contrast, a shape branching into two or more parts and an elongated shape are considered as non-ideal shapes.

Figure 28:
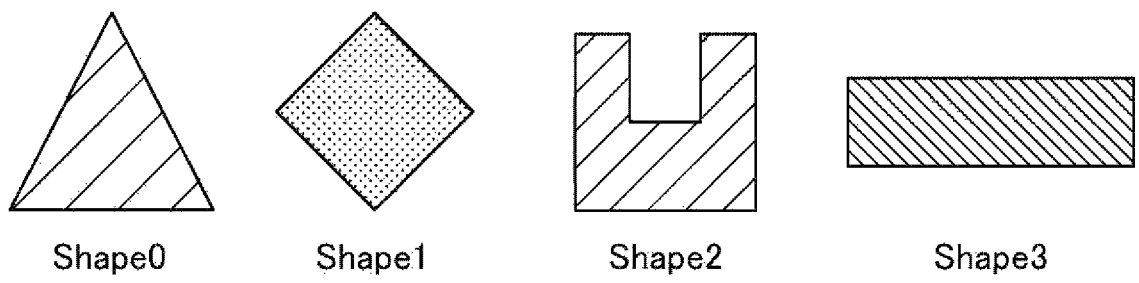
FIG. 28 is a view explaining examples of a reference shape.

Therefore, the epidermis shape distribution analyzer 153 sets, for example, Shape 0 to Shape 3 shown in FIG. 28 as reference shapes. The reference shapes Shape 0 and Shape 1 are a triangle shape and a diamond shape, respectively, which are similar to the ideal shapes of the ridges. On the other hand, the reference shapes Shape 2 and Shape 3 are a shape branching into two parts and an elongated shape, respectively, which are similar to the non-ideal shapes of the ridges.

Then, the epidermis shape distribution analyzer 153 selects one reference shape which has not been yet compared with the ridge region.

In Step S122, the epidermis shape distribution analyzer 153 selects a comparison region. Specifically, the epidermis shape distribution analyzer 152 selects one ridge region which has not been yet compared with the reference shape and sets the ridge region as the comparison region.

In Step S123, the epidermis shape distribution analyzer 153 calculates a shape difference between the reference shape and the comparison region. Note that the same method as in the calculation of the difference between the reference region and the comparison region of the ridge region in Step S103 of FIG. 25, which is described above, is used for the calculation of the difference at this time.

In Step S124, the epidermis shape distribution analyzer 153 integrates differences. Specifically, the epidermis shape distribution analyzer 153 adds a newly calculated difference to the previously calculated integrated value of the differences of the ridge regions from the current reference shape.

In Step S125, the epidermis shape distribution analyzer 153 determines whether or not a ridge region not compared with the current reference shape remains. If it is determined that the ridge region not compared with the current reference shape remains, processing returns to Step S122.

After that, until it is determined in Step S125 that the ridge region not compared with the current reference shape does not remain, processing of from Steps S122 to S125 is repeatedly performed.

If it is determined in Step S125 that the ridge region not compared with the current reference shape does not remain, processing proceeds to Step S126.

In Step S126, the epidermis shape distribution analyzer 153 determines whether or not the reference shape not compared remains. If it is determined that the reference shape not compared remains, processing returns to Step S121.

After that, until it is determined in Step S126 that the reference shape not compared does not remain, processing of from Steps S121 to S126 is repeatedly performed. As a result, as shown in the following Expression (16), a cumulative addition value $Diff_i$ of the differences of the shapes of the ridge regions from the reference shapes is calculated.

$$Diff_i = \sum_{j=0}^{N_{ridge}} D(S_i, R_j) \qquad (16)$$

Note that $S_i$ indicates a reference shape with a value of ID being i.

If it is determined in Step S126 that the reference shape not compared does not remain, processing proceeds to Step S127.

In Step S127, the epidermis shape distribution analyzer 153 calculates a shape ratio of the ridge regions. Specifically, the epidermis shape distribution analyzer 153 calculates an epidermis shape distribution information $ShapeRatio_i$ indicating the shape ratio of the ridge regions according to the following Expression (17).

$$ShapeRatio_i = \frac{Diff_i}{\sum_{i=0}^{N_{RS}-1} Diff_i} \qquad (17)$$

Where $N_{RS}$ indicates the total number of reference shapes.

Thus, the epidermis shape distribution information $ShapeRatio_i$ indicates a ratio at which the ridge regions have shapes similar to the reference shape with the value of ID being i.

The epidermis shape distribution analyzer 152 supplies the epidermis shape distribution information $ShapeRatio_i$ to the texture evaluator 104.

After that, epidermis shape distribution analysis processing 2 is terminated.

Referring back to FIG. 22, in Step S84, the epidermis directivity analyzer 154 analyzes the directivity of the epidermis pattern by applying an edge filter of four directions of, for example, 0 degrees, 45 degrees, 90 degrees, and 135 degrees to the noise-removed epidermis image. More specifically, the epidermis directivity analyzer 154 calculates an epidermis directivity evaluation value $Eeval_{direction}$ indicating uniformity of the distribution of the edge directions of the ridge regions, which takes a value smaller than 1 when the edge directions of the ridge regions are not uniformly distributed in the four directions.

Then, acquired-element analysis processing is terminated and processing returns to texture analysis processing in FIG. 19 and proceeds to the calculation of the texture evaluation value by the texture evaluator 104 in the subsequent Step S44.

<Calculation of Texture Evaluation Value>

Next, the calculation of the texture evaluation value, which is performed by the texture evaluator 104, will be described in detail.

For example, the texture evaluator 104 calculates a texture evaluation value $eval1_{total}$ according to the following Expression (18).

$$eval1_{total} = Eeval_{size} * Eeval_{shape} * Eeval_{direction} \qquad (18)$$

The texture evaluation value $eval1_{total}$ increases as the uniformity of the sizes of the ridges, uniformity of the shapes of the ridges, and uniformity of the directions of the ridges increases, that is, as the texture is generally smoother (uniformity of texture increases). Further, the uniformity of the sizes of the ridges, the uniformity of the shapes of the ridges, and the uniformity of the directions of the ridges change in an acquired manner due to aging, health condition, skin care, and the like. Thus, the texture evaluation value $eval1_{total}$ is an index for evaluating the uniformity of the skin texture, which changes in an acquired manner.

This uniformity of the texture significantly influences the appearance of the skin like the fineness of the texture. That is, if the texture is generally smooth even when the texture is fine, the appearance of the skin is bad. On the other hand, if the texture is generally smooth even when the texture is not fine, the appearance of the skin is good.

Instead of the texture evaluation value $eval1_{total}$ or together with the texture evaluation value $eval1_{total}$, the texture evaluation value $eval2_{total}$ may be calculated according to the following Expression (19).

$$eval2_{total} = Eeval_{size} * Eeval_{shape} * Eeval_{direction} * ShapeRatio_{ideal} \quad (19)$$

$ShapeRatio_{ideal}$ is calculated according to the following Expression (20), for example.

$$ShapeRatio_{ideal} = ShapeRatio_0 * ShapeRatio_1 \quad (20)$$

$ShapeRatio_0$ is ShapeRatio with respect to the reference shape Shape0 of the triangle in FIG. 28. $ShapeRatio_1$ is ShapeRatio with respect to the reference shape Shape1 of the diamond in FIG. 28. That is, $ShapeRatio_{ideal}$ shows a ratio at which the ridge regions have triangle or diamond shapes considered as the ideal shapes.

Thus, $eval2_{total}$ increases as the ratio at which the ridges have the ideal shapes increases in addition to the uniformity of the texture. Therefore, the texture evaluation value $eval2_{total}$ is an index for evaluating the acquired elements that affect the skin texture condition in more details in comparison with the texture evaluation value $eval1_{total}$.

Then, the texture evaluator 104 supplies the evaluation result of the skin texture condition to the evaluation result presentation unit 83. At this time, the texture evaluator 104 supplies the evaluation result presentation unit 83 not only with the texture evaluation value $eval1_{total}$ and the texture evaluation value $eval2_{total}$, but also with the evaluation values used when the texture evaluation value $eval1_{total}$ and the texture evaluation value $eval2_{total}$ are calculated.

<Presentation Example of Texture Evaluation Result>

A presentation example of the texture evaluation result by the evaluation result presentation unit 83 will be described.

Figure 29:
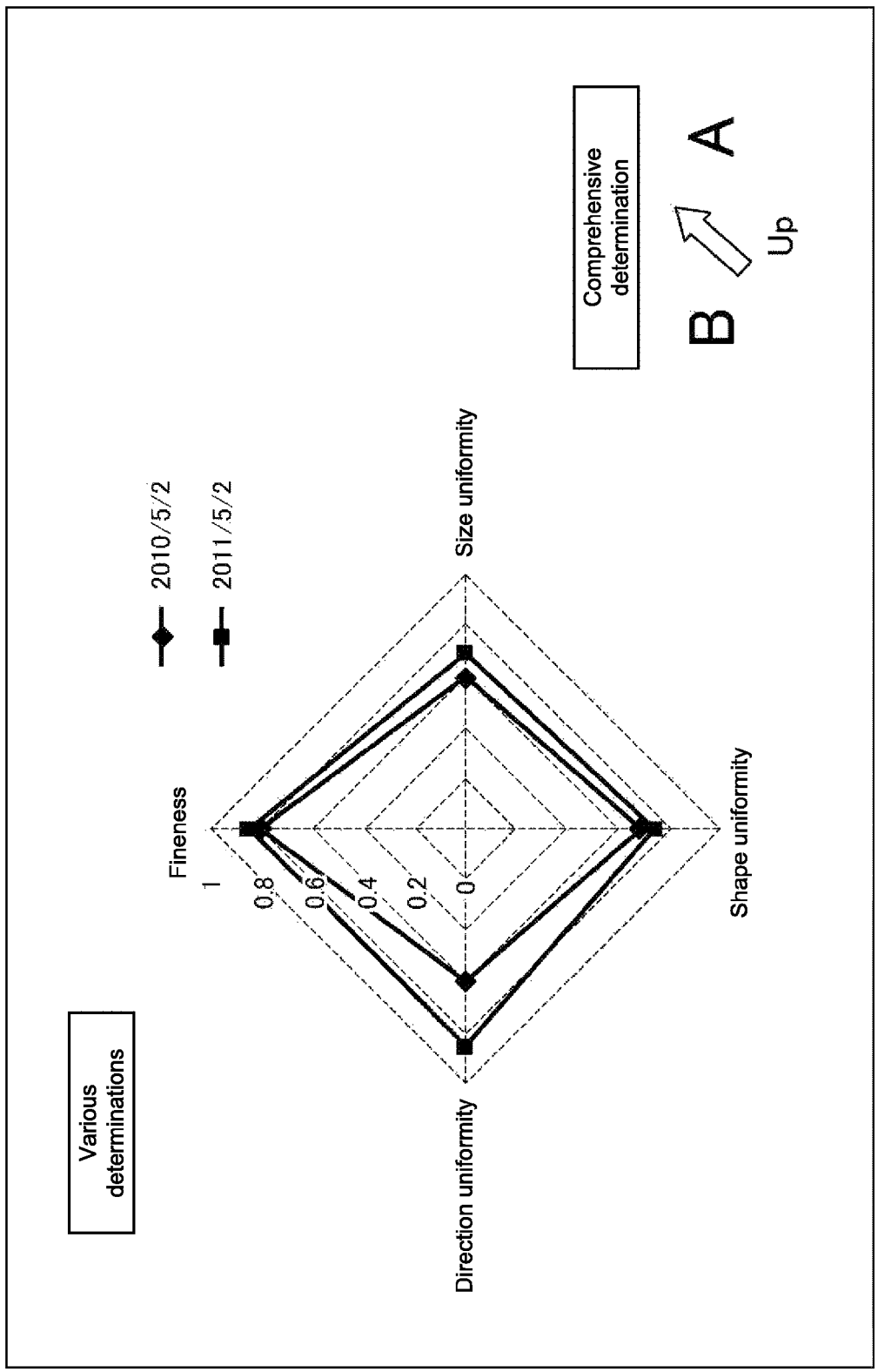
FIG. 29 is a view showing a presentation example of a texture evaluation result.

For example, the evaluation result presentation unit 83 causes the display apparatus 13 to display a screen shown in FIG. 29. In this example, a radar chart showing current evaluation values of the uniformity of the sizes of the ridges, the uniformity of the shapes of the ridges, the uniformity of the distribution of the directions of the ridges, and the fineness of the texture with the current evaluation values being individually compared with preceding evaluation values. As the values in this radar chart, an epidermis size distribution evaluation value $Eeval_{size}$, an epidermis shape distribution evaluation value $Eeval_{shape}$, an epidermis directivity evaluation value $Eeval_{direction}$, and a number-of-ridges evaluation value $Eeval_{num}$ are used.

Further, in this example, a change in comprehensive determination between the preceding skin texture condition and the current skin texture condition is shown. This comprehensive determination value is displayed based on a result obtained by comparing the texture evaluation value $eval3_{total}$ obtained by comprehensively evaluating, for example, the epidermis size distribution evaluation value $Eeval_{size}$, the epidermis shape distribution evaluation value $Eeval_{shape}$, the epidermis directivity evaluation value $Eeval_{directio}$, and the number-of-ridges evaluation value $Eevalnum$ with the preceding texture evaluation value $eval3_{total}$.

With this, the examinee can immediately know the skin condition and also know a change in the skin condition from the preceding one.

Figure 30:
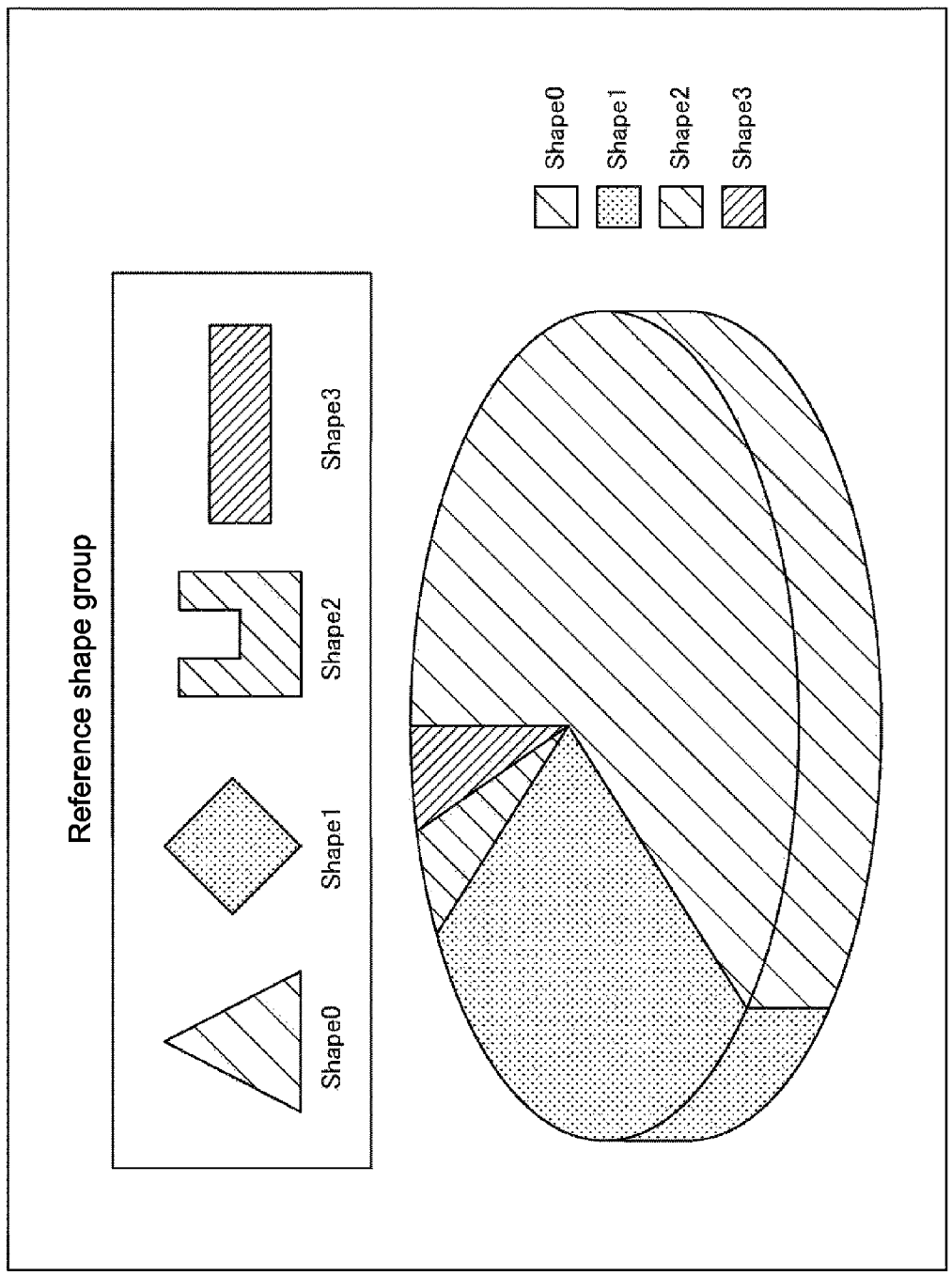
FIG. 30 is a view showing another presentation example of the texture evaluation result.

Alternatively, as shown in FIG. 30, based on the epidermis shape distribution information $ShapeRatio_i$, a circle graph indicating a distribution of shapes of the ridges may also be presented.

In the above-mentioned manner, in texture analysis processing by the texture analyzer 82, it is possible to separately evaluate the acquired characteristics and inherent characteristics of the skin texture condition. In addition, it is possible to evaluate the skin texture condition in more details based on the acquired characteristics and the inherent characteristics.

According to skin texture analysis processing described above, it is possible to evaluate the skin surface condition using the unpolarized light image and the orthogonal polarized light image that are acquired by the imaging apparatus 11, and hence it is possible to evaluate a skin surface condition with a low-cost configuration.

3. Third Embodiment

<Block Diagram of Imaging System>

Figure 31:
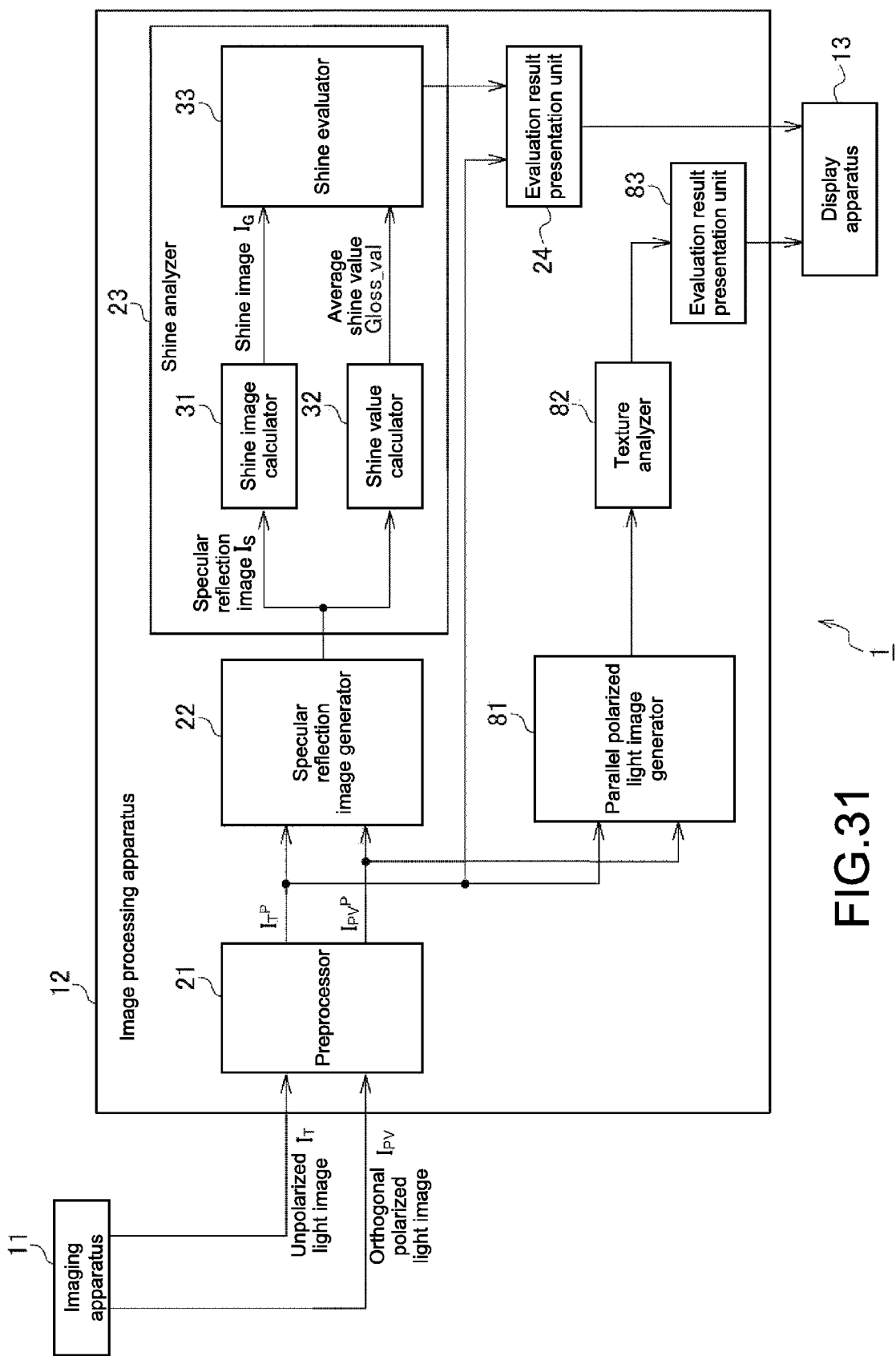
FIG. 31 is a block diagram showing an imaging system according to a third embodiment of the present disclosure.

FIG. 31 is a block diagram showing an imaging system according to a third embodiment of the present disclosure.

An imaging system 1 according to the third embodiment is a system serving both a function of evaluating the skin shine in the above-mentioned first embodiment and a function of evaluating the skin texture in the above-mentioned second embodiment.

Thus, an image processing apparatus 12 in FIG. 31 includes a preprocessor 21, a specular reflection image generator 22, a shine analyzer 23, and an evaluation result presentation unit 24 and a parallel polarized light image generator 81, a texture analyzer 82, and an evaluation result presentation unit 83.

The image processing apparatus 12 according to the third embodiment is capable of performing both a process of evaluating the skin shine and a process of evaluating the skin texture using the two kinds of (two) images of the unpolarized light image $I_T$ and the orthogonal polarized light image $I_{PV}$ that are supplied from the imaging apparatus 11.

The image processing apparatus 12 according to the third embodiment may also perform either one of the process of evaluating the skin shine and the process of evaluating the skin texture according to an instruction selected by an operator, initial settings, or the like.

The configurations and operations of the image processing apparatus 12 are the same as those of the above-mentioned first and second embodiments, and hence descriptions thereof will be omitted.

4. Fourth Embodiment

<Block Diagram of Imaging System>

Figure 32:
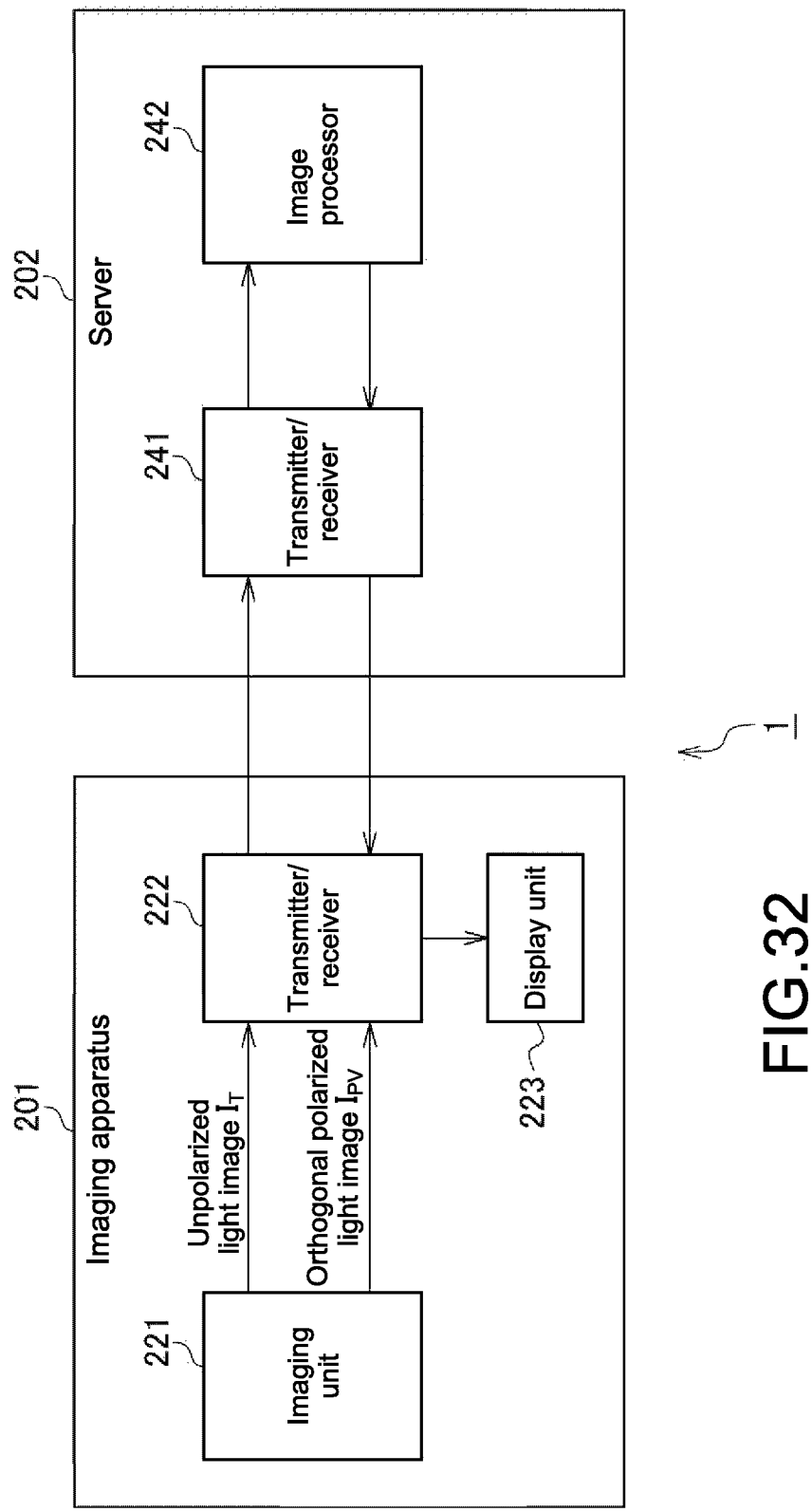
FIG. 32 is a block diagram showing an imaging system according to a fourth embodiment of the present disclosure.

FIG. 32 is a block diagram showing an imaging system according to a fourth embodiment of the present disclosure.

Although the above-mentioned first to third embodiments are embodiments in which the image processing apparatus 12 placed at a closer distance from the imaging apparatus 11 acquires an image signal via a cable or the like and performs image processing, the functions performed by the image processing apparatus 12 may be performed by a cloud server or the like.

The imaging system 1 shown in FIG. 32 represents a configuration example in which the above-mentioned functions performed by the image processing apparatus 12 are performed by the cloud server.

The imaging system 1 according to the fourth embodiment includes an imaging apparatus 201 and a server 202.

The imaging apparatus 201 includes an imaging unit 221, a transmitter/receiver 222, and a display unit 223. The server 202 includes a transmitter/receiver 241 and an image processing unit 242.

The imaging unit 221 has the same functions as those of the imaging apparatus 11 described above. The imaging unit 221 captures two kinds of (two) images of an unpolarized light image $I_T$ and an orthogonal polarized light image $I_{PV}$ as skin images and supplies these images to the transmitter/receiver 222.

The transmitter/receiver 222 transmits the two images supplied from the imaging unit 221 to the server 202 via a network such as a local area network (LAN) and the Internet.

The transmitter/receiver 222 receives information indicating a skin shine evaluation result or a skin texture evaluation result, which is transmitted from the server 202, and supplies the information to the display unit 223.

The display unit 223 displays, based on the information supplied from the transmitter/receiver 222, the skin shine evaluation result or the skin texture evaluation result.

The transmitter/receiver 241 of the server 202 receives the two kinds of (two) images of the unpolarized light image $I_T$ and the orthogonal polarized light image $I_{PV}$ that are transmitted from the transmitter/receiver 222 of the imaging apparatus 201.

The transmitter/receiver 241 acquires the information indicating the skin shine evaluation result or the skin texture evaluation result, which is obtained by image processing in the image processing unit 242, and transmits the information to the imaging apparatus 201.

The image processing unit 242 has the same functions as those of the image processing apparatus 12 according to any of the above-mentioned first to third embodiments and performs the skin shine evaluation or the skin texture evaluation based on the two kinds of images of the unpolarized light image $I_T$ and the orthogonal polarized light image $I_{PV}$.

In the above description, all the functions of the image processing apparatus 12 according to the first to third embodiments are performed by the image processing unit 242 of the server 202. However, the contents of processing performed by the server 202 may be appropriately set. Specifically, the server 202 may perform some of the functions of the image processing apparatus 12. In this case, sharing of image processing on the imaging apparatus 11 side and image processing on the server 202 side may be arbitrarily set.

<Configuration Example of Computer>

The series of image processing described above may be performed by hardware or may be performed by software. If the series of image processing are performed by software, programs configuring the software are installed on a computer. The computer includes a computer incorporated in dedicated hardware, a general-purpose personal computer, for example, capable of executing various functions by installing various programs, and the like.

Figure 33:
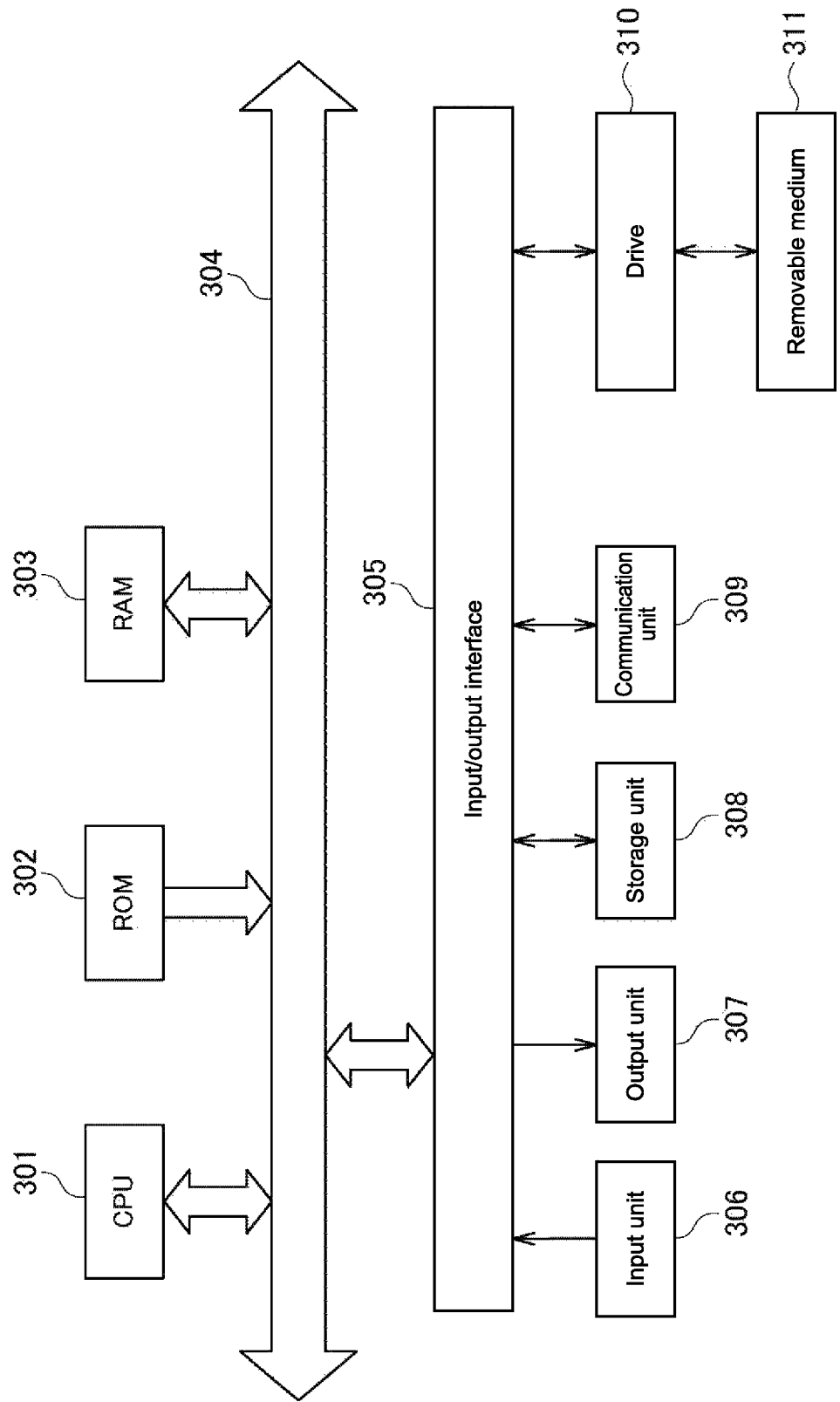
FIG. 33 is a block diagram showing a configuration example of a computer according to an embodiment of the present disclosure.

FIG. 33 is a block diagram showing a configuration example of hardware of a computer that executes the series of image processing described above according to the programs.

In the computer, a central processing unit (CPU) 301, a read only memory (ROM) 302, and a random access memory (RAM) 303 are connected to one another via a bus 304.

In addition, an input/output interface 305 is connected to the bus 304. An input unit 306, an output unit 307, a storage unit 308, a communication unit 309, and a drive 310 are connected to the input/output interface 305.

The input unit 306 includes a keyboard, a mouse, a microphone, and the like. The output unit 307 includes a display, a speaker, and the like. The storage unit 308 includes a hard disk, a non-volatile memory, and the like. The communication unit 309 includes a network interface and the like. The drive 310 drives a removable medium 311 such as a magnetic disk, an optical disc, a magneto-optical disk, and a semiconductor memory.

In the thus configured computer, by the CPU 301 loading the programs stored in, for example, the storage unit 308 into the RAM 303 via the input/output interface 305 and the bus 304 and executing the loaded programs, the series of image processing described above are performed.

In the computer, the programs can be installed on the storage unit 308 via the input/output interface 305 by the removable medium 311 being mounted on the drive 310. Alternatively, the programs may be received by the communication unit 309 via a wired or wireless communication medium such as a local area network, the Internet, and digital satellite broadcasting and installed on the storage unit 308. In addition, the programs may be installed on the ROM 302 and the storage unit 308 in advance.

Herein, the steps described in the flowcharts may be performed in time series following the described order, of course, and do not need to be necessarily processed in time series. The steps may be performed in parallel or at a necessary timing, for example, when a call is performed.

Note that the "system" set forth in the present specification means a collection of a plurality of components (apparatuses, modules (components), etc.) and all components may or do not need to be included in a single casing. Thus, both a plurality of apparatuses housed in respective casings and connected to one another via a network and a single apparatus including a plurality of modules housed in a single casing are systems.

Embodiments of the present disclosure are not limited to the above-mentioned embodiments and various modifications can be made without departing from the gist of the present disclosure.

For example, it is possible to employ an embodiment combining all or some of the above-mentioned embodiments.

For example, the present disclosure may take a cloud computing configuration in which a single function is shared and cooperatively processed by a plurality of apparatuses over a network.

Further, the steps described with reference to the flowcharts may performed by a single apparatus or may be shared and performed by a plurality of apparatuses.

In addition, if a single step includes a plurality of processes, the plurality of processes included in the single step may be performed by a single apparatus or may be shared and performed by a plurality of apparatuses.

Note that the effects set forth in the present specification are merely exemplary and not limited and effects other than those set forth in the present specification may be provided.

Note that the present disclosure may also take the following configurations.

(1) An imaging apparatus, including:

an unpolarized light-emitting portion configured to emit light having an unpolarized component;

a polarized light-emitting portion configured to emit light having a predetermined polarized component via a first polarization filter; and an imaging element configured to image a subject, which is irradiated with light by one of the unpolarized light-emitting portion and the polarized light-emitting portion, through a second polarization filter, the first polarization filter and the second polarization filter having polarization directions in an orthogonal relationship to each other, the imaging element being further configured to image the subject irradiated with light by the unpolarized light-emitting portion and the subject irradiated with light by the polarized light-emitting portion in a time division manner and output an unpolarized light image and an orthogonal polarized light image that are obtained as a result of imaging.

(2) The imaging apparatus according to (1), in which
the unpolarized light-emitting portion and the polarized light-emitting portion include a plurality of unpolarized light-emitting portions and a plurality of polarized light-emitting portions that are arranged in a point symmetrical manner with the imaging element being a center.

(3) The imaging apparatus according to (1) or (2), in which
the unpolarized light-emitting portion and the polarized light-emitting portion include a plurality of unpolarized light-emitting portions and a plurality of polarized light-emitting portions that are arranged in an annular manner with the imaging element being a center.

(4) An imaging method of an imaging apparatus, the imaging apparatus including
an unpolarized light-emitting portion configured to emit light having an unpolarized component,
a polarized light-emitting portion configured to emit light having a predetermined polarized component through the first polarization filter, and
an imaging element configured to image a subject, which is irradiated with light by one of the unpolarized light-emitting portion and the polarized light-emitting portion, through a second polarization filter, the first polarization filter and the second polarization filter having polarization directions in an orthogonal relationship to each other, the method including by the imaging apparatus:
imaging the subject irradiated with light by the unpolarized light-emitting portion and the subject irradiated with light by the polarized light-emitting portion in a time division manner; and
outputting an unpolarized light image and an orthogonal polarized light image.

(5) An image processing apparatus, including
a specular reflection image generator configured to
acquire an unpolarized light image and an orthogonal polarized light image that are captured by an imaging apparatus including
an unpolarized light-emitting portion configured to emit light having an unpolarized component,
a polarized light-emitting portion configured to emit light having a predetermined polarized component through the first polarization filter, and
an imaging element configured to image a subject, which is irradiated with light by one of the unpolarized light-emitting portion and the polarized light-emitting portion, through a second polarization filter, the first polarization filter and the second polarization filter having polarization directions in an orthogonal relationship to each other, and
generate, from the unpolarized light image and the orthogonal polarized light image, a specular reflection image being an image having a specular reflection component.

(6) The image processing apparatus according to (5), in which
the specular reflection image generator includes a gain multiplier configured to multiply a gain with the orthogonal polarized light image,
a subtractor configured to subtract the orthogonal polarized light image after the gain multiplication from the unpolarized light image to generate a first difference image, and
a clipper configured to clip the first difference image to have a luminance value in a predetermined range.

(7) The image processing apparatus according to (5) or (6), further including
a shine analyzer configured to analyze skin shine using the specular reflection image generated by the specular reflection image generator.

(8) The image processing apparatus according to (7), in which
the shine analyzer includes
a shine image calculator configured to calculate, based on the specular reflection image, a shine image being an image indicating an amount of sebum of an examinee.

(9) The image processing apparatus according to (7) or (8), in which
the shine analyzer includes a shine value calculator configured to calculate, based on the specular reflection image, an amount of sebum of an examinee.

(10) The image processing apparatus according to (9), in which
the shine analyzer further includes a shine evaluator configured to calculate, based on the amount of sebum calculated by the shine value calculator, a shine evaluation value for evaluating shine of an examinee.

(11) The image processing apparatus according to any one of (7) to (10), further including
a result presentation unit configured to present an analysis result of shine of skin of an examinee by the shine analyzer, in which
the result presentation unit is configured to present, as the analysis result, a shine image and an amount of sebum of the skin of the examinee.

(12) The image processing apparatus according to any one of (5) to (11), further including:
a preprocessor that is provided at a previous stage of the specular reflection image generator and configured to adjust luminance levels of the unpolarized light image and the orthogonal polarized light image and supply the unpolarized light image and the orthogonal polarized light image after the adjustment to the specular reflection image generator.

(13) An imaging processing method of an image processing apparatus, including:
acquiring an unpolarized light image and an orthogonal polarized light image that are captured by an imaging apparatus including
an unpolarized light-emitting portion configured to emit light having an unpolarized component,
a polarized light-emitting portion configured to emit light having a predetermined polarized component through the first polarization filter, and
an imaging element configured to image a subject, which is irradiated with light by one of the unpolarized light-emitting portion and the polarized light-emitting portion, through a second polarization filter, the first polarization filter and the second polarization filter having polarization directions in an orthogonal relationship to each other; and
generating a specular reflection image being an image having a specular reflection component from the unpolarized light image and the orthogonal polarized light image.

(14) A program that causes a computer to execute a process, the computer being configured to process an unpolarized light image and an orthogonal polarized light image that are captured by an imaging apparatus including an unpolarized light-emitting portion configured to emit light having an unpolarized component, a polarized light-emitting portion configured to emit light having a predetermined polarized component through the first polarization filter, and an imaging element configured to image a subject, which is irradiated with light by one of the unpolarized light-emitting portion and the polarized light-emitting portion, through a second polarization filter, the first polarization filter and the second polarization filter having polarization directions in an orthogonal relationship to each other, the process including generating a specular reflection image being an image having a specular reflection component from the unpolarized light image and the orthogonal polarized light image.

(15) An image processing apparatus, including a parallel polarized light image generator configured to acquire an unpolarized light image and an orthogonal polarized light image that are captured by an imaging apparatus including an unpolarized light-emitting portion configured to emit light having an unpolarized component, a polarized light-emitting portion configured to emit light having a predetermined polarized component through the first polarization filter, and an imaging element configured to image a subject, which is irradiated with light by one of the unpolarized light-emitting portion and the polarized light-emitting portion, through a second polarization filter, the first polarization filter and the second polarization filter having polarization directions in an orthogonal relationship to each other, and generate a parallel polarized light image being an image having a parallel polarized component from the unpolarized light image and the orthogonal polarized light image.

(16) The image processing apparatus according to (15), in which the parallel polarized light image generator includes a gain calculator configured to calculate a gain, a gain multiplier configured to multiply the gain with the orthogonal polarized light image, a subtractor configured to subtract the orthogonal polarized light image after the gain multiplication from the unpolarized light image to generate a second difference image, and an offset adder configured to add a predetermined offset value to the second difference image.

(17) The image processing apparatus according to (15) or (16), further including a texture analyzer configured to analyze skin texture using the parallel polarized light image generated by the parallel polarized light image generator.

(18) The image processing apparatus according to any one of (15) to (17), further including:

a preprocessor that is provided at a previous stage of the parallel polarized light image generator and configured to adjust luminance levels of the unpolarized light image and the orthogonal polarized light image and supply the unpolarized light image and the orthogonal polarized light image after the adjustment to the parallel polarized light image generator.

(19) An imaging processing method of an image processing apparatus, including:

acquiring an unpolarized light image and an orthogonal polarized light image that are captured by an imaging apparatus including an unpolarized light-emitting portion configured to emit light having an unpolarized component, a polarized light-emitting portion configured to emit light having a predetermined polarized component through the first polarization filter, and an imaging element configured to image a subject, which is irradiated with light by one of the unpolarized light-emitting portion and the polarized light-emitting portion, through a second polarization filter, the first polarization filter and the second polarization filter having polarization directions in an orthogonal relationship to each other; and generating a parallel polarized light image being an image having a parallel polarized component from the unpolarized light image and the orthogonal polarized light image.

(20) A program that causes a computer to execute a process, the computer being configured to process an unpolarized light image and an orthogonal polarized light image that are captured by an imaging apparatus including an unpolarized light-emitting portion configured to emit light having an unpolarized component, a polarized light-emitting portion configured to emit light having a predetermined polarized component through the first polarization filter, and an imaging element configured to image a subject, which is irradiated with light by one of the unpolarized light-emitting portion and the polarized light-emitting portion, through a second polarization filter, the first polarization filter and the second polarization filter having polarization directions in an orthogonal relationship to each other, the process including generating a parallel polarized light image being an image having a parallel polarized component from the unpolarized light image and the orthogonal polarized light image.

It should be understood by those skilled in the art that various modifications, combinations, sub-combinations and alterations may occur depending on design requirements and other factors insofar as they are within the scope of the appended claims or the equivalents thereof.

What is claimed is:

1. An imaging apparatus, comprising:
   an unpolarized light-emitting portion configured to emit light having an unpolarized component;
   a polarized light-emitting portion configured to emit light having a predetermined polarized component via a first polarization filter; and
   an imaging element configured to image a subject, which is irradiated with light by one of the unpolarized light-emitting portion and the polarized light-emitting portion, through a second polarization filter, the first polarization filter and the second polarization filter having polarization directions in an orthogonal relationship to each other, the imaging element being further configured to image the subject irradiated with light by the unpolarized light-emitting portion and the subject irradiated with light by the polarized light-emitting portion in a time division manner and output an unpolarized light image and an orthogonal polarized light image that are obtained as a result of imaging.

2. The imaging apparatus according to claim 1, wherein the unpolarized light-emitting portion and the polarized light-emitting portion include a plurality of unpolarized light-emitting portions and a plurality of polarized light-emitting portions that are arranged in a point symmetrical manner with the imaging element being a center.

3. The imaging apparatus according to claim 1, wherein the unpolarized light-emitting portion and the polarized light-emitting portion include a plurality of unpolarized light-emitting portions and a plurality of polarized light-emitting portions that are arranged in an annular manner with the imaging element being a center.

4. An imaging method of an imaging apparatus, the imaging apparatus including an unpolarized light-emitting portion configured to emit light having an unpolarized component, a polarized light-emitting portion configured to emit light having a predetermined polarized component through the first polarization filter, and an imaging element configured to image a subject, which is irradiated with light by one of the unpolarized light-emitting portion and the polarized light-emitting portion, through a second polarization filter, the first polarization filter and the second polarization filter having polarization directions in an orthogonal relationship to each other, the method comprising by the imaging apparatus:

imaging the subject irradiated with light by the unpolarized light-emitting portion and the subject irradiated with light by the polarized light-emitting portion in a time division manner; and outputting an unpolarized light image and an orthogonal polarized light image.

5. An image processing apparatus, comprising a specular reflection image generator configured to acquire an unpolarized light image and an orthogonal polarized light image that are captured by an imaging apparatus including an unpolarized light-emitting portion configured to emit light having an unpolarized component, a polarized light-emitting portion configured to emit light having a predetermined polarized component through the first polarization filter, and an imaging element configured to image a subject, which is irradiated with light by one of the unpolarized light-emitting portion and the polarized light-emitting portion, through a second polarization filter, the first polarization filter and the second polarization filter having polarization directions in an orthogonal relationship to each other, and generate, from the unpolarized light image and the orthogonal polarized light image, a specular reflection image being an image having a specular reflection component.

6. The image processing apparatus according to claim 5, wherein the specular reflection image generator includes a gain multiplier configured to multiply a gain with the orthogonal polarized light image, a subtractor configured to subtract the orthogonal polarized light image after the gain multiplication from the unpolarized light image to generate a first difference image, and a clipper configured to clip the first difference image to have a luminance value in a predetermined range.

7. The image processing apparatus according to claim 5, further comprising a shine analyzer configured to analyze skin shine using the specular reflection image generated by the specular reflection image generator.

8. The image processing apparatus according to claim 7, wherein the shine analyzer includes a shine image calculator configured to calculate, based on the specular reflection image, a shine image being an image indicating an amount of sebum of an examinee.

9. The image processing apparatus according to claim 7, wherein the shine analyzer includes a shine value calculator configured to calculate, based on the specular reflection image, an amount of sebum of an examinee.

10. The image processing apparatus according to claim 9, wherein the shine analyzer further includes a shine evaluator configured to calculate, based on the amount of sebum calculated by the shine value calculator, a shine evaluation value for evaluating shine of an examinee.

11. The image processing apparatus according to claim 7, further comprising a result presentation unit configured to present an analysis result of shine of skin of an examinee by the shine analyzer, wherein the result presentation unit is configured to present, as the analysis result, a shine image and an amount of sebum of the skin of the examinee.

12. The image processing apparatus according to claim 5, further comprising:

a preprocessor that is provided at a previous stage of the specular reflection image generator and configured to adjust luminance levels of the unpolarized light image and the orthogonal polarized light image and supply the unpolarized light image and the orthogonal polarized light image after the adjustment to the specular reflection image generator.

13. An imaging processing method of an image processing apparatus, comprising:

acquiring an unpolarized light image and an orthogonal polarized light image that are captured by an imaging apparatus, wherein the imaging apparatus includes an unpolarized light-emitting portion configured to emit light having an unpolarized component, a polarized light-emitting portion configured to emit light having a predetermined polarized component through the first polarization filter, and an imaging element configured to image a subject, which is irradiated with light by one of the unpolarized light-emitting portion and the polarized light-emitting portion, through a second polarization filter, the first polarization filter and the second polarization filter having polarization directions in an orthogonal relationship to each other; and generating a specular reflection image being an image having a specular reflection component from the unpolarized light image and the orthogonal polarized light image.

14. A non-transitory computer readable medium storing a program that is executable by a computer to perform operations comprising:

acquiring an unpolarized light image and an orthogonal polarized light image that are captured by an imaging apparatus, wherein the imaging apparatus includes an unpolarized light-emitting portion configured to emit light having an unpolarized component, a polarized light-emitting portion configured to emit light having a predetermined polarized component through the first polarization filter, and an imaging element configured to image a subject, which is irradiated with light by one of the unpolarized light-emitting portion and the polarized light-emitting portion, through a second polarization filter, the first polarization filter and the second polarization filter having polarization directions in an orthogonal relationship to each other; and generating a specular reflection image being an image having a specular reflection component from the unpolarized light image and the orthogonal polarized light image.

15. An image processing apparatus, comprising
a parallel polarized light image generator configured to
acquire an unpolarized light image and an orthogonal polarized light image that are captured by an imaging apparatus including
an unpolarized light-emitting portion configured to emit light having an unpolarized component,
a polarized light-emitting portion configured to emit light having a predetermined polarized component through the first polarization filter, and
an imaging element configured to image a subject, which is irradiated with light by one of the unpolarized light-emitting portion and the polarized light-emitting portion, through a second polarization filter, the first polarization filter and the second polarization filter having polarization directions in an orthogonal relationship to each other, and
generate a parallel polarized light image being an image having a parallel polarized component from the unpolarized light image and the orthogonal polarized light image.

16. The image processing apparatus according to claim 15, wherein
the parallel polarized light image generator includes
a gain calculator configured to calculate a gain,
a gain multiplier configured to multiply the gain with the orthogonal polarized light image,
a subtractor configured to subtract the orthogonal polarized light image after the gain multiplication from the unpolarized light image to generate a second difference image, and
an offset adder configured to add a predetermined offset value to the second difference image.

17. The image processing apparatus according to claim 15, further comprising
a texture analyzer configured to analyze skin texture using the parallel polarized light image generated by the parallel polarized light image generator.

18. The image processing apparatus according to claim 15, further comprising:

a preprocessor that is provided at a previous stage of the parallel polarized light image generator and configured to adjust luminance levels of the unpolarized light image and the orthogonal polarized light image and supply the unpolarized light image and the orthogonal polarized light image after the adjustment to the parallel polarized light image generator.

19. An imaging processing method of an image processing apparatus, comprising:

acquiring an unpolarized light image and an orthogonal polarized light image that are captured by an imaging apparatus, wherein the imaging apparatus includes an unpolarized light-emitting portion configured to emit light having an unpolarized component, a polarized light-emitting portion configured to emit light having a predetermined polarized component through the first polarization filter, and an imaging element configured to image a subject, which is irradiated with light by one of the unpolarized light-emitting portion and the polarized light-emitting portion, through a second polarization filter, the first polarization filter and the second polarization filter having polarization directions in an orthogonal relationship to each other; and generating a parallel polarized light image being an image having a parallel polarized component from the unpolarized light image and the orthogonal polarized light image.

20. A non-transitory computer readable medium storing a program that is executable by a computer to perform operations comprising:

acquiring an unpolarized light image and an orthogonal polarized light image that are captured by an imaging apparatus, wherein the imaging apparatus includes an unpolarized light-emitting portion configured to emit light having an unpolarized component, a polarized light-emitting portion configured to emit light having a predetermined polarized component through the first polarization filter, and an imaging element configured to image a subject, which is irradiated with light by one of the unpolarized light-emitting portion and the polarized light-emitting portion, through a second polarization filter, the first polarization filter and the second polarization filter having polarization directions in an orthogonal relationship to each other; and generating a parallel polarized light image being an image having a parallel polarized component from the unpolarized light image and the orthogonal polarized light image.

* * * * *